United States Patent
Ecker et al.

(10) Patent No.: US 12,275,043 B2
(45) Date of Patent: Apr. 15, 2025

(54) CLEANING ITEMS TO BE CLEANED, WHICH HAVE AT LEAST ONE CAVITY, IN A CONVEYOR WASHER

(71) Applicant: MEIKO Maschinenbau GmbH & Co. KG, Offenburg (DE)

(72) Inventors: Engelbert Ecker, Offenburg (DE); Bruno Gaus, Offenburg (DE); Wendelin Hils, Rheinmünster (DE); Thomas Näger, Offenburg (DE); Marc Scherer, Hofstetten (DE); Marijan Simundic, Ohlsbach (DE)

(73) Assignee: MEIKO Maschinenbau GmbH & Co. KG, Offenburg (DE)

( * ) Notice: Subject to any disclaimer, the term of this patent is extended or adjusted under 35 U.S.C. 154(b) by 396 days.

(21) Appl. No.: 17/782,881

(22) PCT Filed: Dec. 4, 2020

(86) PCT No.: PCT/EP2020/084601
§ 371 (c)(1),
(2) Date: Jun. 6, 2022

(87) PCT Pub. No.: WO2021/110897
PCT Pub. Date: Jun. 10, 2021

(65) Prior Publication Data
US 2023/0030171 A1   Feb. 2, 2023

(30) Foreign Application Priority Data
Dec. 6, 2019   (DE) ................. 10 2019 219 094.4

(51) Int. Cl.
*B08B 3/02*   (2006.01)
*A61L 2/18*   (2006.01)
(Continued)

(52) U.S. Cl.
CPC ............... *B08B 3/022* (2013.01); *A61L 2/18* (2013.01); *B08B 9/0813* (2013.01); *B08B 13/00* (2013.01);
(Continued)

(58) Field of Classification Search
CPC ....... B08B 3/022; B08B 9/0813; B08B 13/00; A61L 2/18; A61L 2202/122;
(Continued)

(56) References Cited

U.S. PATENT DOCUMENTS

| 3,881,503 A | 5/1975 | Fox et al. |
| 2013/0319460 A1* | 12/2013 | Schneider ................. A61L 2/14 134/1.1 |

FOREIGN PATENT DOCUMENTS

| CN | 103025444 A | 4/2013 |
| DE | 1174169 B | 7/1964 |

(Continued)

OTHER PUBLICATIONS

International Search Report; European Patent Office; International Application No. PCT/EP2020/084601; Mar. 22, 2021; 5 pages.
(Continued)

*Primary Examiner* — Tinsae B Ayalew
(74) *Attorney, Agent, or Firm* — Taft Stettinius & Hollister LLP

(57) ABSTRACT

The invention relates to an item-to-be-cleaned carrier for the cleaning of items to be cleaned, which have at least one cavity, the cleaning being performed in a conveyor washer. The item-to-be-cleaned carrier can be used in particular for cleaning personal protective equipment. The item-to-be-cleaned carrier comprises at least one base element and at least one nozzle tube, which is connected to the base element. The nozzle tube has at least one inlet opening having at least one catching funnel. The nozzle tube has at
(Continued)

least one outlet nozzle. The nozzle tube tapers, at least in parts, from the inlet opening to the outlet nozzle. The invention further relates to a cleaning system and to a method for cleaning items to be cleaned, which have at least one cavity, using the cleaning system.

12 Claims, 6 Drawing Sheets

(51) Int. Cl.
 *B08B 9/08* (2006.01)
 *B08B 13/00* (2006.01)
(52) U.S. Cl.
 CPC ..... *A61L 2202/122* (2013.01); *A61L 2202/15* (2013.01); *A61L 2202/17* (2013.01); *A61L 2202/24* (2013.01); *A61L 2202/26* (2013.01)
(58) Field of Classification Search
 CPC ............. A61L 2202/15; A61L 2202/17; A61L 2202/24; A61L 2202/26
 USPC .......................................................... 134/72
 See application file for complete search history.

(56) References Cited

FOREIGN PATENT DOCUMENTS

| DE | 2712020 | A1 | 9/1978 |
|---|---|---|---|
| DE | 29822172 | U1 | 2/1999 |
| DE | 20003744 | U1 | 7/2000 |
| DE | 20003743 | U1 | 11/2000 |
| DE | 10020835 | A1 | 11/2001 |
| DE | 102005033618 | B3 | 11/2006 |
| DE | 102007009936 | A1 | 9/2008 |
| DE | 102007012768 | B4 | 1/2009 |
| DE | 102014209765 | A1 | 11/2015 |
| EP | 1088928 | A1 | 4/2001 |
| EP | 0935687 | B1 | 6/2001 |
| EP | 3563940 | A1 | 11/2019 |
| FR | 1333543 | A | 7/1963 |
| GB | 1380740 | A | 1/1975 |
| WO | 2011144518 | A2 | 11/2011 |

OTHER PUBLICATIONS

Chinese Office Action; China National Intellectual Property Administration; Chinese Application No. 202080084600.4; Dec. 8, 2023; pages.

Canadian Office Action; Canadian Intellectual Property Office; Canadian Application No. 3,159,871; Nov. 3, 2023; 6 pages.

International Preliminary Report on Patentability; The International Bureau of WIPO; International Application No. PCT/EP2020/084601; Jun. 9, 2022; 7 pages.

\* cited by examiner

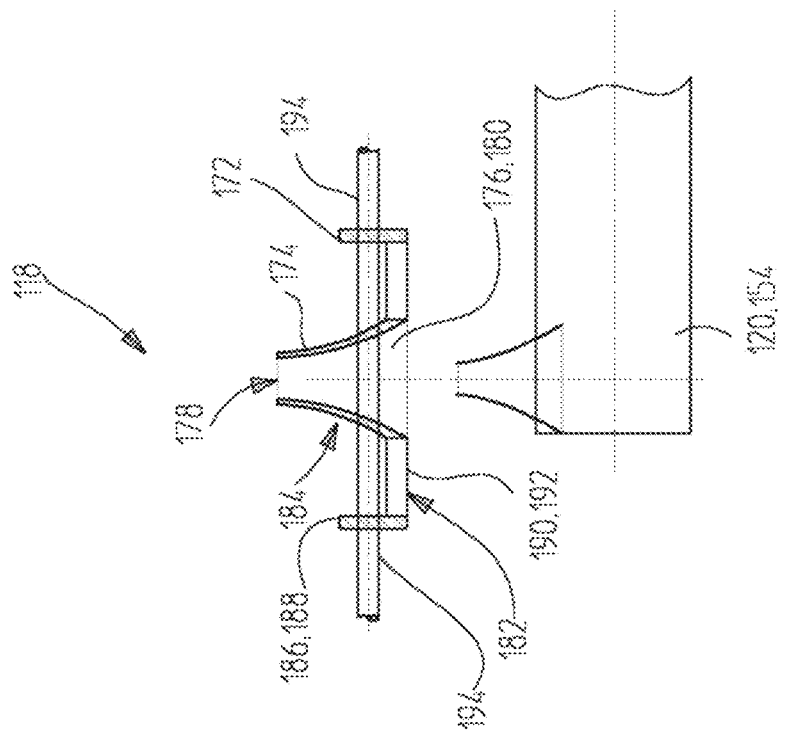
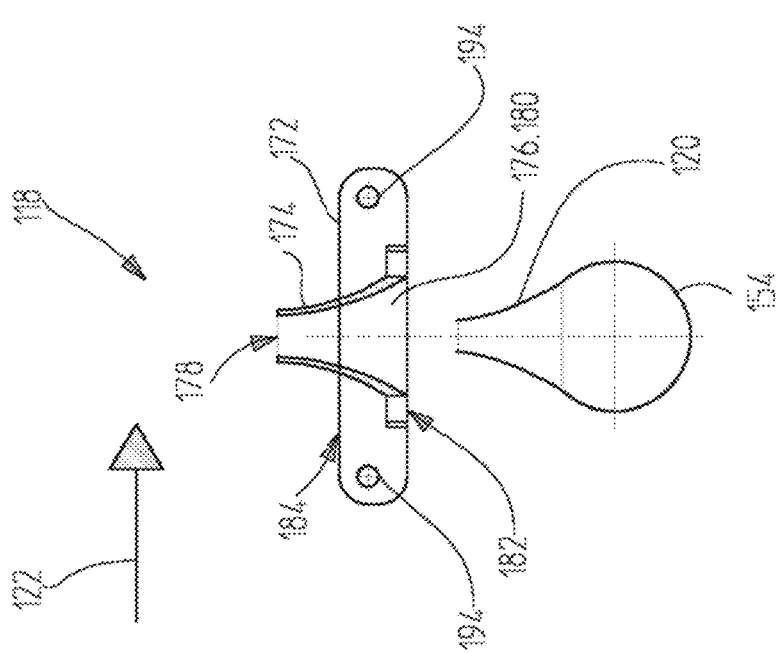

CLEANING ITEMS TO BE CLEANED, WHICH HAVE AT LEAST ONE CAVITY, IN A CONVEYOR WASHER

CROSS-REFERENCE TO RELATED APPLICATIONS

This application is a U.S. National Phase Application of International PCT Application No. PCT/EP2020/084601, which was filed on Dec. 4, 2020, and which claims priority to German Patent Application No. 102019219094.4, which was filed on Dec. 6, 2019. The contents of each of those applications are incorporated herein by reference in their entireties.

TECHNICAL FIELD

The invention relates to a cleaning items carrier, to a cleaning system, and to a method for cleaning items to be cleaned having at least one cavity in a conveyor washer. The invention furthermore relates to the use of the cleaning items carrier according to the invention as well as of the cleaning system for cleaning personal protective equipment. Devices and methods of this type can generally be used in particular for cleaning items which have one or a plurality of cavities such as, for example, one or a plurality of ducts. Protective helmets, respiratory equipment or other component parts of personal protective equipment, in particular component parts of personal equipment which have at least one duct, for example a duct for supplying or discharging breathing air, are to be particularly emphasized here. This here can in particular be personal protective equipment for personnel working in the field of production in a toxic and/or dust-charged environment. Alternatively or additionally, this may also be personal protective equipment such as, for example, respiratory equipment for emergency services such as the fire department, technical disaster relief organizations or emergency paramedics, respiratory equipment for divers, or generally for people in life-threatening or critical working environments, as well as for the armed forces and security forces such as the police. Respiratory equipment in the medical field, for example respirators for the supply of oxygen and for surgery can also use the proposed devices and methods. Other fields of application are also conceivable, for example the use in cleaning other items to be cleaned having at least one cavity, for example bottles, carafes, glasses, or similar items to be cleaned.

TECHNICAL BACKGROUND

Items which have at least one cavity are known from numerous applications. Items which have one or a plurality of ducts, for example for supplying and/or discharging air can be mentioned as examples here. However, other items can in principle be cleaned in this way. The invention will be described hereunder in particular with a view to the particularly important field of cleaning items of personal protective equipment, in particular items having at least one duct for supplying and/or discharging breathing air, without being limited in terms of further potential applications.

In this way, a multiplicity of respiratory equipment for various applications is known from the prior art. To be mentioned here purely by way of example is respiratory equipment such as, for example, respiratory masks or breathing apparatuses which are typically a component part of the personal protective equipment of emergency services, armed forces or security forces. A further important field is occupational safety. Here too, helmets or respiratory masks which have an airflow are used in order to protect personnel from toxic dust or vapor, for example.

These items of personal protective equipment, including the airflow, typically have to be cleaned, sanitized, dried, tested and optionally serviced after each use. All contaminations as a result of use or storage are to be removed by cleaning, so that the respiratory equipment can be provided so as to be macroscopically clean and hygienically perfect, for example for the next step of preparation.

Numerous cleaning devices by means of which respiratory equipment and accessories can be cleaned are known. Reference by way of example may be made to EP 0 935 687 B1, to EP 1 088 928 A1, to DE 200 03 743 U1 and to DE 298 22 172 U1, to DE 10 2005 033 618 B3, to DE 200 03 744 U1, to DE 10 2007 009 936 A1, to DE 10 2007 012 768 B4, to DE 100 20 835 A1, to U.S. Pat. No. 3,881,503 A, to DE 11 74 169 B, or to WO 2011/144518 A2. Cleaning devices by means of which critical items such as, for example, surgical instruments, can be cleaned are also known in principle from other technical fields. In this regard, reference may be made to DE 27 12 020 A1, for example, in which a decontamination system for surgical instruments is described.

Despite the advantages which have been and are achieved by the devices and methods described above, numerous technical challenges remain. In particular in items, for example personal protective equipment, having at least one cavity, in particular at least one airflow duct, one technical challenge lies in cleaning the internal walls of the cavity. It is indeed in principle possible for the cavity to be separately sprayed with cleaning fluid, such as by way of a separate nozzle, for example, or in particular also manually. In practice however, difficulties arise in particular when a high throughput in terms of the items to be cleaned is required. Items of personal protective equipment are present in high volumes, for example, during the deployment of emergency services or else in the industrial sector and in the field of occupational safety. In this way, there are operations in which several hundred, even thousands of, contaminated respiratory masks or other parts of personal protective equipment have to be handled per working shift, every 10 hours, for example. The investment in personnel for manually cleaning volumes of this type would be considerable, and the quality of manual cleaning is moreover often subject to heavy fluctuations.

However, known mask washers, for example according to the design embodiments described above, are typically not capable of cleaning large volumes of items to be cleaned. In contrast, conveyor washers are typically not capable of sufficiently and reliably cleaning cavities, such as arise in particular in the region of the airflow ducts, because only a small proportion of the cleaning fluid enters the cavities, for example the ducts, and even this small proportion doing so unreliably, when the items to be cleaned pass the stationary nozzles. In this way, a plurality of single-chamber mask washers would generally have to be operated in parallel in order to enable the throughput, as a result of which the consumption of resources and the procurement costs would however increase in a linear manner. Moreover, depending on the type and quantity of the contamination of the personal protective equipment, the wastewater from the mask washers would have to be disposed of separately as special waste, as a result of which additional costs and environmental stress could arise. In practice, solutions which are based on conveyor washers also have significant problems. In this way, the connection of a nozzle basket to a supply line of the conveyor washer, described in DE 27 12 020 A1, for example, is associated with high manual complexity in terms of the installation, because installation work is in each case required at the inlet and at the outset of the conveyor washer. Said nozzle baskets also significantly restrict the throughput, and moreover require a high level of complexity in terms of engineering.

OBJECT OF THE INVENTION

It would, therefore, be desirable to provide devices and methods for cleaning items to be cleaned having at least one cavity, that at least largely avoid the disadvantages of known devices and methods of the type mentioned. In particular, the devices and methods are to be able to be used for cleaning personal protective equipment having at least one cavity, for example at least one airflow duct. The items to be cleaned here are to be reliably and safely cleaned also within the cavity while at the same time attaining a high throughput in association with an ideally low complexity in terms of personnel and engineering.

GENERAL DESCRIPTION OF THE INVENTION

This object is addressed by a cleaning items carrier, a cleaning system and a method for cleaning items to be cleaned having at least one cavity in a conveyor washer, and furthermore by the use. The invention furthermore relates to the use of the cleaning items carrier according to the invention as well as of the cleaning system for cleaning personal protective equipment, having the features of independent patent claims. Advantageous refinements which can be implemented individually or in any combination are illustrated in the dependent claims.

In the text which follows, the terms "exhibit", "have", "comprise" or "include" or any grammatical departures therefrom are used non-exclusively. Accordingly, these terms can refer both to situations in which, apart from the features introduced by these terms, no further features are present, and to situations in which one or more further features are present. For example, the expression "A exhibits B", "A has B", "A comprises B" or "A includes B" may refer both to the situation in which, apart from B, no further element is present in A (i.e. to a situation in which A exclusively consists of B), and to the situation in which, in addition to B, one or more further elements are present in A, for example element C, elements C and D or even further elements.

Furthermore, it should be noted that the terms "at least one" and "one or more" and grammatical modifications of these terms, if they are used in association with one or more elements or features and are intended to express the fact that the element or feature can be provided singly or multiply, generally are used only once, for example when the feature or element is introduced for the first time. When the feature or element is subsequently mentioned again, the corresponding term "at least one" or "one or more" is generally no longer used, without restricting the possibility that the feature or element may be provided singly or multiply.

Furthermore, in the text which follows, the terms "preferably", "in particular", "for example" or similar terms are used in conjunction with optional features, without alternative embodiments being restricted thereby. Thus, features which are introduced by these terms are optional features, and the scope of protection of the claims, and in particular of the independent claims, is not intended to be restricted by these features. Thus, as a person skilled in the art will appreciate, the invention can also be carried out using other configurations. In a similar way, features which are introduced by "in one embodiment of the invention" or by "in one exemplary embodiment of the invention" are understood as optional features, without alternative configurations or the scope of protection of the independent claims being intended to be restricted thereby. Furthermore, all possibilities of combining the features introduced by these introductory expressions with other features, be they optional or non-optional features, are intended to remain unaffected by these introductory expressions.

Proposed in a first aspect of the present invention is a cleaning items carrier for cleaning items to be cleaned in a conveyor washer, wherein the items to be cleaned have at least one cavity. The cleaning items carrier can in particular be used for cleaning cavities in personal protective equipment. However, other fields of application are possible in principle.

The term "cleaning items carrier", as it is used here, is a broad term which is to be taken to have its customary and commonly used meaning as it is understood by a person skilled in the art. The term is not limited to any special or adapted meaning. The term, without limitation, can relate in particular to a fundamentally arbitrary device which is specified to hold items to be cleaned during cleaning, in particular in a predefined spatial positioning and/or orientation. The cleaning items carrier per se may be cleaned herein. The cleaning items carrier can be entirely or partially produced from at least one plastics material, for example. The cleaning items carrier can in particular be produced by means of at least one additive manufacturing method, for example by at least one 3D printing method and/or by plastics material laser sintering. Alternatively or additionally however, other materials and/or production methods are also possible, for example metallic materials.

The term "cleaning" as used here is likewise a broad term which is to be taken to have its customary and commonly used meaning as it is understood by a person skilled in the art. The term is not limited to any special or adapted meaning. The term, without limitation, can relate in particular to a procedure in which items to be cleaned are relieved from macroscopic and/or microscopic contaminations adhering thereto, and/or in which contaminations of this type are at least partially removed. Additionally, a disinfecting effect can optionally be implemented.

The term "items to be cleaned" as used here is likewise a broad term which is to be taken to have its customary and commonly used meaning as it is understood by a person skilled in the art. The term is not limited to any special or adapted meaning. The term, without limitation, can in particular relate to arbitrary items which are to be subjected to cleaning. As mentioned, these here can in particular be items which have at least one cavity, in particular items to be cleaned having at least one duct, in particular at least one duct having at least one entry opening and, for example, also at least one exit opening. The items to be cleaned, as will yet be explained in more detail hereunder, can in particular comprise personal protective equipment. The items to be cleaned can thus in particular comprise at least one respiratory mask, also referred to as a respirator. The term "respiratory mask" as used here is likewise a broad term which is to be taken to have its customary and commonly used meaning as it is understood by a person skilled in the art. The term is not limited to any special or adapted meaning. The term, without limitation, can in particular relate to a device which is specified to entirely or partially cover the face of a user, in particular a mouth region and/or nose region. The covering can in particular serve for protecting the respiratory system of the user from harmful substances and/or for introducing breathing gases into the respiratory system and/or for discharging breathing gases from the respiratory system. Moreover, the respiratory mask can cover further regions of the face and/or of the head of the user, for example the eyes or an upper region of the head. Accordingly, the respiratory mask can in particular also have at least one transparent viewing window. The respiratory mask can in particular have at least one duct for an airflow of breathing air, in particular fresh air and/or exhaust air. The respiratory mask can be configured so as to be entirely or partially rigid, or else entirely or partially flexible. In this way, the respiratory mask can also be entirely or partially designed as a helmet, for example. Alternatively or additionally, the respiratory mask can also be entirely or partially flexible, as is the case with full-protection masks for emergency services. Furthermore, the respiratory mask can have at least one fixing for fastening to the head of the user, for example at least one strap, at least one fixing band, or at least one fastening which is composed of a plurality of bands. The respiratory mask can have at least one opening, for example, and can be specified to enable the supply of air or breathing gas, for example. For example, the respiratory mask can have at least one thread for connecting a breathing gas supply. Furthermore, the respiratory mask can have at least one exhalation valve, for example. Moreover, the respiratory mask can comprise further components.

The term "washer", generally also referred to as "cleaning device", as used here is a broad term which is to be taken to have its customary and commonly used meaning as it is understood by a person skilled in the art. The term is not limited to any special or adapted meaning. The term, without limitation, can in particular relate to a device which is specified to relieve items to be cleaned of macroscopic or else microscopic contaminations adhering thereto, and to at least partially remove contaminations of this type. Additionally, a disinfecting effect can optionally be implemented.

Accordingly, the term "conveyor washer" as used here is a broad term which is to be taken to have its customary and commonly used meaning as is understood by a person skilled in the art. The term is not limited to any special or adapted meaning. The term, without limitation, can in particular relate to a washer in the context of the above definition, which has at least one transport device. The conveyor washer, as will yet be explained in more detail hereunder, can in particular have at least one cleaning chamber, for example at least one cleaning tunnel, in which the items to be cleaned are impinged with at least one cleaning fluid, in particular by means of at least one impingement device, as will likewise be explained in yet more detail hereunder. The transport device can be specified to transport the items to be cleaned through the cleaning chamber.

The cleaning items carrier comprises at least one base element. The term "base element" as is used here is a broad term which is to be taken to have its customary and commonly used meaning as is understood by a person skilled in the art. The term is not limited to any special or adapted meaning. The term, without limitation, can in particular relate to an element which is specified to carry, to position or, in any other way, to mechanically support one or a plurality of further elements. The base element can in particular be entirely or partially designed as a flat and/or plate-shaped element. For example, the base element can be entirely or partially designed as a flat, mesh-shaped element. Examples will be explained in yet more detail hereunder.

The base element can be entirely or partially produced from plastics material, for example. A production which completely or partially uses metallic materials is also possible in principle.

The cleaning items carrier furthermore comprises at least one nozzle tube having at least one entry opening and at least one exit nozzle. This at least one nozzle tube is connected to the base element. The nozzle tube can penetrate the base element, for example. Alternatively or additionally however, the nozzle tube can also be completely or partially integrated in the base element, and/or be held by the base element. For example, the nozzle tube can penetrate the base element from a side on which the entry opening is disposed to the side on which the exit nozzle is disposed. For example, the entry opening can be disposed on a lower side of the base element, and the exit nozzle can be disposed on an upper side, the latter being opposite the lower side of the base element. Alternatively however, the entry opening can also be disposed on at least one longitudinal side, for example, or else on the upper side per se. Without any limitation in terms of further potential design embodiments, it is assumed hereunder that the entry opening is disposed on the lower side of the base element and the exit nozzle is disposed on the upper side, the latter being opposite the lower side of the base element, and that the nozzle tube penetrates the base element.

As explained, the nozzle tube has at least one entry opening. This entry opening has at least one funnel trap. The nozzle tube at least in portions tapers from the entry opening toward the exit nozzle.

The term "nozzle" as used here is a broad term which is to be taken to have its customary and commonly used meaning as is understood by a person skilled in the art. The term is not limited to any special or adapted meaning. The term, without limitation, can in particular relate to a device which has at least one opening in a fluid-conducting element, for example a tube or a nozzle arm from which fluid, in particular as a jet, can exit the fluid-conducting element. The opening can be designed as a round bore, for example, or else as a bore having a polygonal, oval or linear cross section. Other cross sections are also possible. A nozzle here can have a single opening or else a plurality of openings. In this way, a single jet can form on the nozzle, for example, or else a plurality of parallel or else non-parallel jets, for example a jet bundle.

The term "exit nozzle" as used here is accordingly likewise a broad term which is to be taken to have its customary and commonly used meaning as is understood by a person skilled in the art. The term is not limited to any special or adapted meaning. The term, without limitation, can in particular relate to a nozzle in the context of the previous definition, said nozzle being provided in the nozzle tube and through which cleaning fluid that enters the nozzle tube by way of the funnel trap can exit again.

The term "nozzle tube" as used here is a broad term which is to be taken to have its customary and commonly used meaning as is understood by a person skilled in the art. The term is not limited to any special or adapted meaning. The term, without limitation, can in particular relate to a hollow member, for example a tube, a duct or a duct structure, which has at least one nozzle opening from which a fluid medium, for example as a jet, can exit. For example, the nozzle tube can be produced entirely or partially from at least one plastics material. Alternatively or additionally however, metallic materials are also possible, for example. As explained above, the nozzle tube can be designed so as to be separate from the base element, or can also be entirely or completely integrated in the latter, or be held by the base element.

As explained above, the base element has in particular at least one lower side and at least one upper side. The upper side can in particular be the side on which the items to be cleaned are received, whereas the lower side can face the transport device, for example. The upper side and the lower side can be mutually parallel sides, for example. The base element can be designed as a plate-shaped element, for example, having a flat upper side and a flat lower side.

The term "funnel trap" as used here is a broad term which is to be taken to have its customary and commonly used meaning as is understood by a person skilled in the art. The term is not limited to any special or adapted meaning. The term, without limitation, can in particular relate to a funnel-shaped device at the entry of a cavity or tube, said funnel-shaped device being specified to direct fluid media into the cavity and/or the tube. The funnel trap here, in terms of the cross section or equivalent diameter thereof, can taper uniformly or non-uniformly. As explained above, the nozzle tube at least in portions tapers from the entry opening toward the exit nozzle. The funnel trap here can be part of this tapered nozzle tube. The tapering of the nozzle tube can take place uniformly, for example in that a diameter or an equivalent diameter forms a monotonously or strictly monotonously decreasing function of a distance from the entry opening to the exit opening. Alternatively however, the nozzle tube can also taper only in one or a plurality of portions. In turn, a widening on the exit nozzle is furthermore also possible, for example for forming a jet.

The cleaning items carrier can in particular be designed in one or a plurality of the following ways: a chain link in a transport chain of a transport device of a conveyor washer; a cleaning basket, wherein the base element forms part of the basket base of the cleaning basket. In this way, the cleaning items carrier can also be entirely or partially integrated in a transport chain of the transport device. Alternatively, the cleaning items carrier, for example as a cleaning basket, can also be placed onto the transport device, for example a transport belt or a transport chain.

As explained above, the nozzle tube on the exit nozzle can in particular have jet-forming properties. In particular, the cleaning items carrier can have at least one jet-forming element which is specified to form a flow of the cleaning fluid exiting the exit nozzle. This jet-formation can comprise: deflecting, bundling, widening, imparting a rotating pulse, splitting or other types of jet-forming, or else combinations of the types mentioned. The flow-forming element can in particular be selected from the group composed of: a funnel; a nozzle; a baffle; a pipeline; a swirl-inducing element.

As explained above, the cleaning items carrier can in particular be entirely or partially integratable in a link chain. In particular, the base element can be entirely or partially integratable in this link chain, wherein this link chain can be a component part of the transport device of the conveyor washer, for example. This integration in the link chain can be temporary and releasable, or else permanent. Furthermore, only parts of the cleaning items carrier can in particular also be integratable in the link chain, for example only the base element, wherein one or a plurality of further parts that are connectable to the base element can be released from the base element again, for example at the outlet of the conveyor washer. The base element can in particular at least in part be configured as a chain link of a link chain, in particular having shaped elements in which are situated at least two, preferably four, bores through which the belt bars of the transport belt, or of the transport chain, respectively, can be guided.

As explained above, the nozzle tube can be configured so as to taper completely or partially. In this way it is also possible that the nozzle tube is designed so as to be shaped as a funnel from the entry opening toward the exit nozzle, for example.

Furthermore, the entry opening can in particular have an equivalent diameter which is larger than a diameter or equivalent diameter of the exit nozzle. In particular, the entry opening can have an equivalent diameter which is larger than an equivalent diameter of the exit nozzle by a factor of at least 1.3, in particular by a factor of at least 1.5, in particular by a factor of at least 2.

The entry opening can be of a round design, wherein a round design is not mandatory. In particular, the entry opening can also be configured so as to be elongate, as will be explained in yet more detail hereunder, in particular so as to take into account a movement of the cleaning items carrier relative to at least one ejection nozzle disposed so as to be locationally fixed in the conveyor washer. Overall, the entry opening can in particular have a design selected from the group composed of: a circular design; an oval design, in particular an oval design having a longitudinal extent in a transport direction of the conveyor washer; a polygonal design.

The nozzle tube, in particular on the lower side of the base element, can terminate so as to be flush with the base element. In this way, a collision between the nozzle tube and component parts of the conveyor washer can be avoided in that the nozzle tube does not project beyond the lower side, for example. However, the nozzle tube on the upper side can protrude beyond the base element. In this way, the nozzle tube thereon can in particular form a port by way of which cleaning fluid can invade the cavity of the items to be cleaned. A mouth of this port can form the exit nozzle, for example, the latter being able to be moved so as to be congruent with an opening of the cavity of the items to be cleaned, so as to inject the cleaning fluid directly or indirectly into the opening.

As explained above, the entry opening of the nozzle tube can in particular be disposed on the lower side of the base element. Alternatively or additionally however, other arrangements for the at least one entry opening are possible. In this way, at least one entry opening can also be disposed on at least one lateral wall of the cleaning items carrier, in particular on at least one longitudinal wall which is disposed parallel to a transport direction of the conveyor washer, for example. Furthermore, a disposal on the upper side of the cleaning items carrier is also possible in principle, for example on the upper side of the base element. Overall, the at least one entry opening can thus in particular be selected from the group composed of: an entry opening disposed on the lower side of the base element; an entry opening disposed on a longitudinal side of the base element; an entry opening disposed on the upper side of the base element. In principle however, other design embodiments are also possible.

The base element can be designed as a solid, plate-shaped element without openings. However, for the purpose of straining the cleaning fluid as well as for further facilitating the cleaning procedure, it can be advantageous for the cleaning items carrier and in particular the base element to have one or a plurality of openings. In this way, the cleaning items carrier and/or the base element can in particular be completely or partially designed as a mesh. The base element in particular can at least be partially designed as a mesh. In this instance, the nozzle tube can be connected to a frame of the base element by way of mesh partitions, for example.

The nozzle tube can in particular extend so as to be substantially perpendicular to the base element, for example in relation to the plane of the base element. Here, an angular position of exactly 90° may arise, or else a deviation from 90°, for example by not more than 20°. The nozzle tube can be designed as a straight nozzle tube, having a straight tube axis. Alternatively or additionally however, the nozzle tube in one or a plurality of portions can also be configured so as to be curved, for example having a curved tube axis.

As explained above, the base element can in particular be designed so as to be substantially flat. In this way, the base element can have a plate-shaped design, for example. For example, the base element can have a basic shape of a rectangle, having a constant thickness. As explained above, this plate shape can also be a mesh shape.

As explained above, the base element can function as a carrier for one or a plurality of further elements of the cleaning items carrier. These elements can be fixedly or releasably connected to the base element. In particular, at least one rack can be attached to the base element. This rack which may be produced from a plastics material and/or metallic material, for example, can serve a plurality of purposes. In this way, this rack can provide a mounting for the items to be cleaned, for example, and/or a fixing for the items to be cleaned or parts of the latter. Alternatively or additionally, the rack can also form a frame. The base element can form a flat bearing face, for example, and the rack can be connected to the base element so as to be removable therefrom. In this way, the base element and the rack conjointly can form a cleaning basket. The rack can in particular be connected to the base element so as to be removable therefrom.

As explained above, the rack can form at least one mounting for the items to be cleaned. In this way, the rack can form, for example, at least one mounting for a helmet and/or a respiratory mask. The frame here can assume additional tasks. In this way, the rack can furthermore form or have, for example, at least one mounting for a visor of the helmet. This mounting can in particular be specified to hold the visor at a predefined angular position relative to the remaining part of the helmet. One or a plurality of helmets and/or one or a plurality of respiratory masks can be received in the rack.

When cleaning personal protective equipment, situations can arise in which not all regions of the items to be cleaned are allowed to be impinged with cleaning fluid. Thus, in particular, more complex helmets are known, in which valves or else electronic components are not allowed to come into contact with cleaning fluid. In this way, the cleaning items carrier can have, for example, at least one closure element which is disposed so as to be movable in relation to the base element and which is specified to close at least one opening of the items to be cleaned during cleaning and while the items to be cleaned are impinged with cleaning fluid. This at least one opening can in particular be selected from the group composed of an electric connector opening and an airflow opening. The closure element can be produced, for example, from a deformable, in particular flexible material, for example silicone or rubber. The closure element can be connected to the base element in particular by way of at least one flexible connection element, for example a cord and/or a flexible, elongate plastics material web. Other design embodiments are also possible.

The cleaning items carrier can in particular have at least one identifier. The term "identifier" as used here is a broad term which is to be taken to have its customary and commonly used meaning as is understood by a person skilled in the art. The term is not limited to any special or adapted meaning. The term, without limitation, can in particular relate to a device which can be connected to another device or another element and which permits identification of the other device or the other element. This identification here can in particular take place automatically. The at least one identifier can in particular be selected from the group composed of: a metallic identifier; an inductive identifier; an RFID identifier; a graphic identifier, in particular a barcode and/or QR code. In principle however, other identifiers can also be used.

Proposed in a further aspect of the present invention is a cleaning system which is specified for cleaning items to be cleaned having at least one cavity, in particular for cleaning personal protective equipment. The term "cleaning system" as used here is a broad term which is to be taken to have its customary and commonly used meaning as is understood by a person skilled in the art. The term is not limited to any special or adapted meaning. The term, without limitation, can in particular relate to a system which is specified for cleaning items to be cleaned. The term "system" as used here is likewise a broad term which is to be taken to have its customary and commonly used meaning as is understood by a person skilled in the art. The term is not limited to any special or adapted meaning. The term, without limitation, can in particular relate to a unit assembled from at least two components, wherein the components are specified to functionally interact in order to achieve at least one purpose of the system. The components here can be mechanically and/or electrically, in particular reversibly, connected to one another The cleaning system comprises the following components:
I. at least one conveyor washer, comprising:
   at least one cleaning chamber;
   at least one impingement device for impinging the items to be cleaned in the cleaning chamber with at least one cleaning fluid;
   at least one transport device for transporting the items to be cleaned from an inlet of the conveyor washer, through the cleaning chamber, to an outlet of the conveyor washer; and
II. at least one cleaning items carrier according to the present invention, for example according to one or a plurality of the design embodiments described above and/or according to one or a plurality of the embodiments yet to be described in more detail hereunder.

The items to be cleaned here are able to be received on the cleaning items carrier in such a manner that the cavity of the items to be cleaned is connected to the exit nozzle of the cleaning items carrier. The cleaning items carrier by means of the transport device is transportable through the cleaning chamber. The impingement device has at least one stationery ejecting nozzle. This at least one ejecting nozzle in at least one position of the cleaning items carrier is positioned relative to the cleaning items carrier in such a manner that cleaning fluid exiting the ejecting nozzle enters the funnel trap of the nozzle tube.

The term "cleaning chamber" as used here is a broad term which is to be taken to have its customary and commonly used meaning as is understood by a person skilled in the art. The term is not limited to any special or adapted meaning. The term, without limitation, can in particular relate to a completely or partially closed chamber within which the cleaning procedure can be completely or partially carried out. The cleaning chamber can in particular have at least one housing which entirely or partially encloses the cleaning chamber. A single cleaning chamber can be provided here, or else a plurality of cleaning chambers can be provided, for example sequentially, in principle. In particular, the cleaning chamber can be entirely or partially designed as a tunnel, for example as a tunnel having an inlet opening and an outlet opening. Accordingly, the terms "inlet" and "outlet" can relate to regions of the conveyor washer and/or of the transport device of the conveyor washer in which the items to be cleaned enter the cleaning chamber, or exit the cleaning chamber, respectively. In these regions, the transport device can protrude beyond the cleaning chamber and be freely accessible, for example.

The conveyor washer is specified for impinging the items to be cleaned in the cleaning chamber with at least one cleaning fluid. For this purpose, the conveyor washer can in particular have the at least one impingement device, in particular within the cleaning chamber. The term "impingement device" as used here is a broad term which is to be taken to have its customary and commonly used meaning as is understood by a person skilled in the art. The term is not limited to any special or adapted meaning. The term, without limitation, can in particular refer to a fundamentally arbitrary device by means of which the items to be cleaned within the cleaning chamber can be impinged with the cleaning fluid. The impingement device can in particular comprise at least one nozzle system. Furthermore, the impingement device can comprise at least one pump, as well as at least one line system, for providing cleaning liquid to the nozzle system. For example, a nozzle system and a line system for impinging with cleaning liquid from a tank, as well as at least one corresponding pump, can be provided here. Alternatively or additionally, at least one nozzle system can be impinged directly from a supply line, for example, without a pump being required to this end. One or a plurality of cleaning zones which are sequentially passed through, for example continuously or else discontinuously, by the items to be cleaned, for example, can be provided in the cleaning device. In this way, the items to be cleaned can be transported sequentially through a plurality of cleaning zones in which different types of impingement with cleaning liquid take place, for example one or a plurality of cleaning zones selected from the group composed of: a preliminary clearing zone; a washing zone; a rinsing or clear-rinsing zone, wherein the latter can be subdivided once again into a pump clear-rinsing zone and a downstream fresh water clear-rinsing zone. At least one drying step can furthermore be provided, said drying step—in the case of the items to be cleaned being received so as to be stationary in the one chamber—being disposed downstream of the impingement with the cleaning liquid or—in the case of the conveyor washer—being implemented in a drying zone disposed downstream of the liquid cleaning zones, for example.

The term "cleaning fluid" as is used here is a broad term which is to be taken to have its customary and commonly used meaning as is understood by a person skilled in the art. The term is not limited to any special or adapted meaning. The term, without limitation, can in particular relate to a gas and/or a liquid which, when impacting the items to be cleaned, can develop at least one effect that can be selected from the group composed of a cleaning effect, a disinfecting effect, and a drying effect. The cleaning fluid can in particular comprise at least one aqueous liquid, for example water and/or water having one or a plurality of additives, for example having one or a plurality of cleaning concentrates and/or clear-rinsing agents and/or disinfectants. The cleaning device can be specified to use a single cleaning fluid or else to use a combination of a plurality of cleaning fluids. If a plurality of cleaning fluids are provided, the impingement of the items to be cleaned with the different cleaning fluids can thus take place simultaneously or else sequentially. In this way, the items to be cleaned can be transported sequentially through a plurality of cleaning zones, for example, in which an impingement with different types of cleaning fluids and/or with cleaning fluids of different degrees of purity takes place, for example. Different degrees of purity can be generated, for example, by way of a cascading overflow between different tanks of the conveyor washer, wherein a degree of purity preferably increases in the transport direction.

The term "transport device" as used here is likewise a broad term which is to be taken to have its customary and commonly used meaning as is understood by a person skilled in the art. The term is not limited to any special or adapted meaning. The term, without limitation, can in particular relate to a device which is specified to transport at least one other device or at least one other element, in particular items to be cleaned, and/or to drive a movement of the other device or of the other element. The transport device can in particular comprise at least one drive element, for example at least one drive element which runs in the circuit through the cleaning chamber. The transport device, for example the drive element, can in particular comprise at least one element selected from the group composed of: a transport belt; transport rollers, in particular driven transport rollers; a link chain; a belt conveyor; a latching transport system. The transport here can take place continuously or else discontinuously or in a cycled manner, for example, so that continuously operating conveyor washers or else cycled conveyor washers can be implemented, for example. The transport direction can be, for example, a primary direction of a movement of the items to be cleaned within a cleaning chamber of the conveyor washer. The transport direction can be fixedly predefined or may vary, for example in terms of location or time. For example, the transport direction can be directed from an inlet of the conveyor washer toward an outlet.

As explained above, the items to be cleaned are able to be received on the cleaning items carrier in such a manner that the cavity of the items to be cleaned is connected to the exit nozzle of the cleaning items carrier. In this way, the cleaning items carrier can in particular be designed in such a manner that the items to be cleaned are able to be positioned with an opening of the cavity in front of the exit nozzle. The connection between the exit nozzle of the cleaning items carrier and the cavity can in particular be a fluidic connection so that cleaning fluid from the exit nozzle can be sprayed into the cavity. There can be direct contact between the nozzle tube of the cleaning items carrier and the items to be cleaned here, or there can be a gap between the exit nozzle and the items to be cleaned, so that the cleaning fluid between the exit nozzle and the cavity first passes through a stretch of air, for example. The items to be cleaned can be fixed to the cleaning items carrier, for example by way of force-fitting and/or form-fitting fixing, or the items to be cleaned can also be merely placed on the cleaning items carrier. Various design embodiments are possible.

The cleaning items carrier is able to be transported through the cleaning chamber by means of the transport device. As explained above, this can take place in that, for example, the cleaning items carrier is integrated in the transport device, for example in that the cleaning items carrier is integrated in a link chain of the transport device. Alternatively however, the cleaning items carrier can also be placed, for example, on the transport device, for example on a transport belt. The impingement device has at least one stationery ejecting nozzle. The term "ejecting nozzle" as used here is a broad term which is to be taken at its customary and commonly used meaning as is understood by a person skilled in the art. The term is not limited to any special or adapted meaning. The term, without limitation, can in particular relate to a nozzle which is specified to eject, for example to spray, at least one fluid medium. Accordingly, the ejecting nozzle can interact in particular with the nozzle tube, the latter in this instance acting as a "trap nozzle" and be able to completely or partially trap the fluid medium delivered by the ejecting nozzle. The ejecting nozzle here is configured so as to be stationary. A stationary configuration can in particular be understood to be a configuration in which the ejecting nozzle is disposed so as to be locationally fixed in a reference system of the conveyor washer, or in a reference system in which the conveyor washer rests, for example in that said ejecting nozzle is fixedly connected to a housing of the conveyor washer.

This at least one stationery ejecting nozzle in at least one position of the cleaning items carrier is positioned relative to the cleaning items carrier in such a manner that cleaning fluid exiting the ejecting nozzle enters the funnel trap of the nozzle tube. In this way, the cleaning items carrier by virtue of being transported through the transport device can move continuously or discontinuously relative to the ejecting nozzle, for example, so that the at least one nozzle tube of the cleaning items carrier that acts as a trap nozzle moves relative to the ejecting nozzle. In at least one position of the cleaning items carrier, during the transport thereof through the cleaning chamber by means of the transport device the trap nozzle and the ejecting nozzle are however mutually positioned such that cleaning fluid exiting the ejecting nozzle completely or partially enters the funnel trap of the nozzle tube, for example in that the cleaning fluid sprayed by the ejecting nozzle is completely or partially trapped by the funnel trap of the nozzle tube. For example, when the entry opening is situated on the lower side of the base element, this can take place, for example, when the ejecting nozzle generates at least one upward-directed jet of the cleaning fluid and the entry opening is situated exactly above the ejecting nozzle. Alternatively, analogous positions are possible in the case of a lateral disposal of the entry opening and/or in a disposal on the upper side of the cleaning items carrier, when the ejecting nozzle is correspondingly aligned. As soon as the funnel trap travels past the ejecting nozzle, cleaning fluid can generally be trapped by the funnel trap, wherein the cleaning fluid in this instance preferably has an impetus sufficient for penetrating the nozzle tube and for exiting the exit nozzle with sufficient impetus so as to then enter the cavity of the items to be cleaned and clean the latter. Proceeding from the ejecting nozzle, the cleaning fluid in this instance can thus first penetrate the nozzle tube and subsequently enter the cavity.

The conveyor washer can have one or a plurality of ejecting nozzles. If a plurality of ejecting nozzles are provided, the latter can be disposed in parallel and/or in sequence, thus at the same location along a transport path, for example, or else at different locations along this transport path. In particular, at least two of the ejecting nozzles can interact sequentially with the funnel trap. In this way, for example different cleaning fluids can be injected sequentially into the same funnel trap by means of the ejecting nozzles, for example first a preliminary clearing fluid, subsequently one or a plurality of washing fluids, and subsequently one or a plurality of clear-rinsing fluids. Furthermore, at least one drying fluid, for example drying air, can be sequentially injected.

In general, the at least one ejecting nozzle can be designed to be variable, in particular in terms of the jet direction thereof and/or in terms of the jet shape thereof. The cleaning system can in particular be specified to automatically vary the ejecting nozzle, for example by means of at least one controller.

In general, the at least one ejecting nozzle can thus be designed as a rigid ejecting nozzle, for example having at least one fixedly predefined jet direction and/or jet shape. Alternatively or additionally however, the at least one ejecting nozzle can also be designed to be variable, for example in terms of the at least one jet direction and/or in terms of the jet shape. In this way, the at least one ejecting nozzle, or should a plurality of ejecting nozzles be provided, at least one of the ejecting nozzles can also be specified to vary, for example automatically, a jet direction. For example, the at least one ejecting nozzle can thus be mounted so as to be locationally fixed yet pivotable in the conveyor washer so that said ejecting nozzle can vary the jet direction thereof, for example. The jet direction can be adjusted by a motor, for example, and/or also by a lever construction. In this way, the ejecting nozzle by way of the ejecting jet can be specified, for example, to follow the funnel trap at least along a predefined distance of travel of the cleaning items carrier. Again alternatively or additionally, a jet shape of the at least one ejecting nozzle or, should a plurality of ejecting nozzles be provided, of at least one of the ejecting nozzles can be variable. In this way, a wide jet shape can be adjusted when a cleaning items carrier approaches the ejecting nozzle, for example. When the funnel trap in this instance is situated above the ejecting nozzle, a tight jet shape can be chosen so as to impinge the funnel trap in a targeted manner. When the cleaning items carrier moves further away again, the jet shape can also be widened again. This adjustment of the jet shape can also be automatically performed. The adjustment of the jet shape can take place, for example, by way of a variable jet aperture on the ejecting nozzle, or else by way of changing the nozzle aperture, or piezo elements, for example.

The impingement device of the conveyor washer, additionally to the at least one ejecting nozzle, can furthermore have at least one further nozzle. This at least one further nozzle can be disposed and/or designed in such a manner, for example, that said further nozzle does not interact with the funnel trap. In this way, this ejecting nozzle can impinge at least one external surface of the items to be cleaned with cleaning fluid, for example. In this way, an impingement of the cavity and an impingement of the at least one external surface of the items to be cleaned with cleaning fluid can take place simultaneously, for example, or else in a temporally offset manner. The at least one further nozzle can be designed as a spray nozzle and/or as a nozzle arm, for example. In this way, in addition to the at least one ejecting nozzle, one or a plurality of nozzle arms can in each case be provided above and/or below the items to be cleaned, for example.

The cleaning items carrier can have a single entry opening or else can have a plurality of entry openings. When the cleaning items carrier has a plurality of entry openings, the latter can be connected to the same nozzle tube or else to a plurality of different nozzle tubes. If a plurality of entry openings are provided, the cleaning system can be specified to have different entry openings fluidically interact with different ejecting nozzles, in particular so as to in different treating phases feed different entry openings with cleaning fluid from different ejecting nozzles. Other design embodiments are also possible.

As explained above, the conveyor washer can in particular be selected from the group composed of a belt conveyor washer and a basket conveyor washer. Accordingly, the transport device can have at least one belt, for example, and/or at least one link chain and/or at least one latching transport system. As explained above, other design embodiments are also possible.

The conveyor washer can in particular have at least one sensor for identifying the cleaning items carrier. For example, one or a plurality of sensors selected from the group composed of: an optical sensor; a mechanical sensor; a magnetic sensor; an inductive sensor; an electromagnetic sensor, in particular a RFID Sensor and/or wireless sensor, can be used here. The sensor can directly identify the cleaning items carrier and/or else identify, for example, at least one identifier on or in the cleaning items carrier and/or at least one identifier, for example at least one of the identifiers mentioned above, which is situated on the items to be cleaned, for example directly on the items to be cleaned.

The conveyor washer can in particular have at least one controller. The term "controller" as used here is a broad term which is to be taken at its customary and commonly used meaning as is understood by a person skilled in the art. The term is not limited to any special or adapted meaning. The term, without limitation, can in particular relate to an integral or multiple-part device of the cleaning device, which is specified to completely or partially control by open loop and/or closed loop an operation of the conveyor washer. The controller can in particular be specified to vary, in particular control by open loop and/or closed loop, one or a plurality of operating parameters of the conveyor washer, for example a transport speed, at least one temperature, at least one pressure, at least one pump output, at least one valve position, at least one heating output, or else a combination of two or more of the mentioned operating parameters. The controller can in particular comprise at least one data processing device, for example at least one processor. The controller, in particular in terms of programming, can be specified to control or carry out at least one cleaning program of the conveyor washer, for example. Accordingly, the installation of the controller can be partially implemented by hardware or/also, alternatively or additionally, completely or partially by software. Furthermore, the controller can comprise at least one volatile and/or non-volatile data memory. Furthermore, the controller can comprise at least one interface, for example a human/machine interface, for entering commands and/or outputting information, and/or wireless or wire-bound interface for unidirectionally or bidirectionally exchanging data and/or commands between the conveyor washer and at least one further device. The controller can in particular comprise at least one computer and/or at least one processor. The controller can in particular be a central or peripheral machine controller of the conveyor washer.

The controller can in particular be specified to control an impingement of the ejecting nozzle with cleaning fluid, in a manner according to the identification of the cleaning items carrier. The controller can in particular be specified to activate the impingement only when a cleaning items carrier is situated in the region of the ejecting nozzle. Resources can be saved in this way. The conveyor washer can in particular have at least one valve and/or at least one switch for controlling the impingement with the cleaning fluid.

The at least one sensor of the conveyor washer can in particular have at least one sensor selected from the group composed of: a sensor for identifying magnetic codes on the cleaning items carrier; a sensor for identifying identifiers made of metal on the cleaning items carrier; a reed switch; an inductive proximity sensor; an RFID sensor; a light barrier; an optical proximity sensor; image recognition; an ultrasonic sensor; an electromechanical switch, in particular an electromechanical switch for interacting with at least one cam on the cleaning items carrier.

As explained above, the conveyor washer can in particular have a plurality of cleaning zones. The cleaning zones can in particular be passed through sequentially by the items to be cleaned. The at least one stationary ejecting nozzle can in particular be disposed in at least one of the cleaning zones. The cleaning zones can in particular have at least two cleaning zones selected from the group composed of: a preliminary clearing zone; a washing zone; a clear-rinsing zone, in particular a pump clear-rinsing zone and/or a freshwater clear-rinsing zone. Furthermore, the conveyor washer can have at least one drying zone which is disposed downstream of the cleaning zones. At least one drying nozzle can in particular be disposed in the drying zone. The drying nozzle in at least one position of the cleaning items carrier within the drying zone can be positioned relative to the cleaning items carrier in such a manner that drying air exiting the drying nozzle enters the funnel trap of the nozzle tube. The same funnel trap which has previously been used for liquid cleaning fluid can be used for drying here. Alternatively, at least one other funnel trap can also be provided.

As explained above, the cleaning system can in particular be used for cleaning personal protective equipment. Toxic waste material can in particular make its way into the cleaning fluid when cleaning items of this type. Accordingly, the conveyor washer can in particular have a closed tank system which is preferably not connected to the sewage water system or to the general drain. In this way, the closed tank system can in particular be connected to at least one waste disposal tank for disposing hazardous waste.

Alternatively or additionally, the cleaning system, in particular the conveyor washer, can also have at least one treatment installation and be specified to treat, in particular purify, the cleaning fluid. In this way, the cleaning system, in particular the conveyor washer, can be equipped with one or a plurality of special treatment installations which remove undesirable, in particular toxic, waste material from a cleaning fluid already within the conveyor washer, or even within a treatment zone of the conveyor washer, said special treatment installations being, for example, special filter systems which preferably go beyond the effect of known filter systems for suspended particles in the washers. For example, at least one treatment installation in the form of a fine filter or microfilter, for example in the form of a cloth filter, can be provided. Other design embodiments are also possible.

Apart from the at least one ejecting nozzle, the cleaning system can comprise further nozzles. In this way, the impingement device can comprise, for example, the at least one ejecting nozzle as well as at least one further nozzle, wherein the at least one further nozzle can be used for cleaning regions other than the cavity of the items to be cleaned, for example. Accordingly, the ejecting nozzle and the at least one further nozzle can also be impinged with different types of cleaning fluid. In particular, the at least one cavity can be impinged with a higher quality of cleaning fluid than an external region of the items to be cleaned, for example. In this way, spreading contaminations from at least one external surface of personal protective equipment to regions which are used for guiding breathing gas, for example, can be prevented in that both cleaning fluids are separately used. The at least one further nozzle can thus also be used in a circulating operation, for example, whereas the ejecting nozzle can be impinged with fresh cleaning fluid in a simple throughput operation, for example. The conveyor washer can in particular have at least one filter system for the post-impingement filtering of toxic substances from the cleaning fluid and/or prior to the items to be cleaned being freshly impinged.

The ejecting nozzle, or when a plurality of ejecting nozzles are provided, at least one of the ejecting nozzles, can in particular be disposed below the transport device so as to point upward. The funnel trap of the nozzle tube can in particular also be aligned so as to point downward. The cleaning fluid exiting the ejecting nozzle can enter the funnel trap of the nozzle tube when the funnel trap and the ejecting nozzle are congruent. As explained above however, ejecting nozzles of a different orientation are alternatively or additionally possible, for example ejecting nozzles which impinge an entry opening of a funnel trap on a lateral wall of the cleaning items carrier, and/or ejecting nozzles which impinge an upward-directed entry opening of a funnel trap of the cleaning items carrier.

The ejecting nozzle and the nozzle tube can in particular be specified so as to pass one another without contact. In this way, a minimal spacing between the ejecting nozzle and the nozzle tube can be 0.5 mm to 5 cm. A connection in the form of a connector between the fluid supply and the nozzle tube is thus not required.

As explained above, there are various possibilities in terms of the design embodiment of the transport device. The transport device can thus in particular be selected from the group composed of: a transport belt, wherein the cleaning items carrier, in particular as a basket-shaped cleaning items carrier, is placed on the transport belt; a transport belt, wherein the cleaning items carrier, in particular as a basket-shaped cleaning items carrier, is connected, in particular latched, to the transport belt; as a link chain, wherein the cleaning items carrier as a chain link is integrated in the link chain; a latching transport system, wherein the cleaning items carrier, in particular as a basket-shaped cleaning items carrier, is placed on sliding elements of the latching transport system.

Proposed in a further aspect of the present invention is a method for cleaning items to be cleaned having at least one cavity, wherein the method provides the use of at least one cleaning system according to the present invention, for example according to one or a plurality of the design embodiments described above and/or according to one or a plurality of the embodiments yet to be described in more detail hereunder. The method comprises the steps mentioned in more detail hereunder. These steps can be carried out in the sequence mentioned. However, any other sequence is also possible in principle. Furthermore, two or more of the method steps mentioned can be carried out so as to be temporally overlapping or simultaneous. The method, beyond the steps mentioned, can comprise further method steps which are not mentioned.

The method comprises the following steps:
i) receiving the items to be cleaned on the cleaning items carrier in such a manner that the cavity of the items to be cleaned by means of the exit nozzle of the cleaning items carrier is able to be impinged with at least one cleaning fluid;
ii) transporting the cleaning items carrier through the cleaning chamber by means of the transport device; and;
iii) impinging the items to be cleaned with at least one cleaning fluid by means of the impingement device, wherein in at least one position of the cleaning items carrier relative to the ejecting nozzle cleaning fluid exiting the ejecting nozzle enters the funnel trap of the nozzle tube, passes through the nozzle tube, and from the exit nozzle of the nozzle tube enters the cavity of the items to be cleaned.

In terms of potential design embodiments and definitions, reference may be made to the above description of the cleaning items carrier and/or of the cleaning system.

The cleaning items carrier can in particular be populated with the items to be cleaned outside the conveyor washer. This populating can take place independently of the transport by means of the transport device, for example. Subsequently, the cleaning items carrier and/or a populated part of the latter in the populated form can be introduced into the conveyor washer.

As explained above, the cleaning items carrier can in particular also be configured in multiple parts. The transport device can in particular be configured as a revolving transport device, for example as a revolving transport belt and/or as a revolving link chain. The cleaning items carrier can in particular be transported conjointly with the items to be cleaned through the cleaning chamber by means of the transport device. Subsequently, the items to be cleaned as well as at least part of the items to be cleaned can be removed from the transport device. Optionally however, at least one further part of the cleaning items carrier, in particular the base element, can remain on or in the transport device and by means of the transport device be transported back to the inlet. This design embodiment can be implemented in particular when the base element is designed as a chain element of a link chain, for example, wherein the cleaning items carrier has at least one removable rack on the base element.

As explained above, the items to be cleaned can in particular be fixed in or on the cleaning items carrier. The at least one optional rack can in particular be provided for this fixing. The fixing can in particular take place in such a manner that the at least one cavity of the items to be cleaned is positioned so as to be locationally fixed in relation to the exit nozzle, in particular locationally fixed in such a manner that cleaning fluid exiting the exit nozzle can invade the cavity.

As explained above, the items to be cleaned can in particular comprise at least part of personal protective equipment. In particular, the items to be cleaned can have at least one helmet having at least one visor. This helmet can have at least one airflow duct as the cavity, for example. The helmet can in particular be fixed in the cleaning items carrier. Furthermore optionally, the visor can be fixed at a predefined angular position in the cleaning items carrier.

Proposed in a further aspect of the present invention is the use of the cleaning items carrier and/or of the cleaning system according to the present invention, for example according to one or a plurality of the design embodiments described above and/or according to one or a plurality of the embodiments yet to be described in more detail hereunder. The use provides cleaning of personal protective equipment by means of the cleaning items carrier and/or by means of the cleaning system. The personal protective equipment here can in particular be selected from the group composed of: a respiratory mask; a helmet having at least one airflow duct.

The proposed cleaning items carrier, the proposed cleaning system, the method and the use have numerous advantages in comparison to conventional devices and methods of a similar type.

By means of the present invention, in particular by using the cleaning items carrier having the at least one nozzle tube having at least one funnel trap, it is thus possible to clean a large amount of items to be cleaned with cavities in that a conveyor washer is used. This here can be, for example, a belt conveyor washer or a basket conveyor washer. Depending on the requirements, the transport can take place continuously or else discontinuously. In principle, a continuous transport can be an advantage here because the latter can typically generate a larger cleaning capacity and cleaning output. There are however cases in which discontinuous transport may be helpful or even necessary, for example in order for the items to be cleaned to be in each case treated at specific positions within the conveyor washer or for said items to be cleaned to be subjected to a special treatment, particularly a particularly intensive treatment.

As explained above, the items to be cleaned can in particular be component parts of personal protective equipment. The items to be cleaned can thus comprise respiratory masks or respiratory helmets, for example. In items to be cleaned of this type, as well as in other items to be cleaned having a cavity, it is often to be expected that regions within the items to be cleaned exist which typically can be cleaned only when the items to be cleaned are held, placed or fastened at a defined position within the cleaning chamber, this typically not being the case in conveyor washers. In the proposed solution having the funnel trap on the cleaning items carrier and having the ejecting nozzle on the conveyor washer, fixing of this type of the items to be cleaned relative to the cleaning items carrier can take place, the latter in this instance in turn being able to be transported in a defined manner through the cleaning chamber. Fixing of the items to be cleaned, for example of the helmet, can take place such, for example, that the cavity comes to be congruent with the exit nozzle on the cleaning items carrier. A fixed connection of lines for the supply of fluid is not required. The impingement can take place while the items to be cleaned travel through the cleaning chamber and thus when in motion.

Furthermore, it is also possible to meet the challenge that personal protective equipment in particular has some particularities in terms of cleaning. In this way, helmets typically have a movable visor which during the treatment typically has to be held at a defined position. Furthermore, respiratory air hoses or openings for supplying breathing air can be present on the helmet or on the mask. These openings typically have to be closed during cleaning. Additionally, electrical connectors, for example for supplying a current or for controlling an electric ventilator, can be present on the helmet or on the mask. These connectors likewise have to be typically covered during cleaning so as to avoid any corrosive attack by cleaning chemicals.

The proposed cleaning items carrier can meet these requirements individually or in combination. Said cleaning items carrier can thus in particular be designed to be separate from the transport device and, for cleaning, be introduced into the conveyor washer. Accordingly, the cleaning items carrier can be flexibly adapted to the type of the items to be cleaned, and a set of different cleaning items carriers can be provided, for example, the cleaning items carriers of said set being able to be readily introduced into the conveyor washer when required. The cleaning items carrier can in particular be designed in such a manner that the items to be cleaned, for example the mask or the helmet, prior to cleaning can be fastened to this cleaning items carrier. The items to be cleaned can remain on the cleaning items carrier during the entire cleaning process, for example, and be removed from the cleaning items carrier only upon being completely treated, in particular after passing through the cleaning chamber, for example. Closure elements for the openings to be closed can optionally be fastened to the cleaning items carrier or be integrated in the latter. Additional elements of this type, depending on the embodiment, can also function in a self-acting manner, for example in that at least one opening to be closed and/or an electrical contact are/is closed in a self-acting manner when the items to be cleaned are clamped in the cleaning items carrier.

The cleaning items carrier can be fixedly connected to the transport device of the conveyor washer, for example to a transport belt. Accordingly, said cleaning items carrier per se can entirely or partially be a component part of the transport device. Alternatively, the cleaning items carrier can, for example, also only be placed on the transport device and/or connected to the latter, for example latched in the transport device, and be removed again at the outlet of the conveyor washer. The latter principle can in particular be designed in a manner analogous to the principle of the cleaning baskets in basket conveyor dishwashers. When the cleaning items carrier is embodied so as to be entirely or partially removable, said cleaning items carrier can in particular be populated with the items to be cleaned outside the conveyor washer and then be introduced into the conveyor washer when fully populated.

Depending on the construction height of the cleaning items carrier, it may be expedient, in particular in the case of a belt conveyor washer, that the entire cleaning items carrier, or else only parts thereof, are placed onto the transport device, in particular the transport belt, at the inlet, and removed again at the outlet of the conveyor washer. In this way, the returning transport belt, for example upon deflection, can run without impediment, and without the returning cleaning items carrier requiring an unnecessarily large amount of installation space.

The cleaning items carrier can in particular be furthermore embodied such that said cleaning items carrier can in each case receive only one piece of the items to be cleaned, for example in each case only one mask or one helmet. However, it is also possible for the cleaning items carrier to be designed in such a manner that a plurality of pieces of items to be cleaned, for example two or more helmets, can be received. When viewed in the transport direction of the conveyor washer, these items to be cleaned can be disposed beside one another. Other constellations are also conceivable.

In order to achieve a large throughput in terms of items to be cleaned, it is particularly expedient for a plurality of cleaning items carriers to be simultaneously used within the conveyor washer. If a plurality of cleaning items carriers are provided in the conveyor washer, said cleaning items carriers can be of identical design. However, it is also possible for a plurality of different types of cleaning items carriers to be provided within the conveyor washer and in the cleaning system, for example cleaning items carriers for different types of items to be cleaned.

In general, the at least one cleaning items carrier can have at least one interface so as to interact with the transport device, in particular an interface which is specified to be coupled to the transport device. This here can be, for example, a force-fitting and/or form-fitting coupling. The cleaning items carrier can in particular be hooked or latched into the transport device. Accordingly, the transport device and/or the cleaning items carrier, in particular the interface, can have at least one connection element which is specified to couple, in particular reversibly, the cleaning items carrier to the transport device. This interface, in particular for the cleaning items carrier, can be of a universal design. If a plurality of cleaning items carriers are provided, the latter can have the same interface, for example. Even when a plurality of types of cleaning items carriers are provided in the cleaning system, said cleaning items carriers can have the same interface for coupling to the transport device, for example. In this way, a geometry of the cleaning items carriers that interacts with the transport device of the conveyor washer can generally be identical in each cleaning items carrier. Moreover, the cleaning items carrier, apart from the interface and the geometry thereof, can have at least one further geometry which can be designed differently from one cleaning items carrier to another cleaning items carrier. In this way, this further geometry, which can also be referred to as the primary geometry, can be designed to receive the items to be cleaned and to fix the latter, for example. This primary geometry can in each case be of an individual and different design, depending on the requirement of the items to be cleaned.

It is thus possible to use many different types of cleaning items carriers in the cleaning system. In order to produce different types of cleaning items carriers individually, cost effectively and efficiently, these cleaning items carriers, or parts thereof, for example the parts which contain the primary geometry for fixing the items to be cleaned, can be designed using production methods which in terms of the geometry thereof can be rapidly varied. In this way, the cleaning items carrier, for example, can be entirely or partially produced by at least one additive manufacturing method, for example plastics material laser sintering.

The at least one nozzle tube can generally be designed as at least one fluid-conducting element and can provide a simple or else a complex duct geometry. In this way, the at least one nozzle tube can have one or a plurality of fluid-conducting elements which can be integrated in the cleaning items carrier, in particular the base element, and/or be attached thereto. One or a plurality of cleaning fluids, for example primary cleaning fluids, clear-rinsing fluids or else air for drying, can be expediently directed by way of this at least one nozzle tube and/or be formed as jets by the latter. These fluid-conducting elements can be embodied as, for example, funnels, nozzles, baffles or pipelines, or else as combinations of these elements. Furthermore, one or a plurality of fluid-conducting elements can also be entirely or partially integrated in the transport device. If the cleaning items carrier is entirely or partially integrated in the transport device, for example, one or a plurality of fluid-conducting elements can thus also be fastened to the transport device, for example to the transport belt, or be integrated therein.

In order for the nozzle tube, in particular the fluid system in the cleaning items carrier, to be supplied with cleaning fluid, the nozzle tube has the funnel trap. The latter can trap a fluid jet which is dispensed by a nozzle placed on the conveyor washer, also referred to as the ejecting nozzle, and direct said fluid jet through the further nozzle tube to the exit nozzle. For example, the exit nozzle can be designed as a spray nozzle. In this way, it is possible for the items to be cleaned, including the at least one cavity, to be able to be subjected to a targeted treatment, despite said items to be cleaned being in motion. A plurality of ejecting nozzles can be provided within the conveyor washer here. As a result of a corresponding design embodiment of the funnel trap and the ejecting nozzles, it is typically not required here that the fluid supply to the cleaning items carrier has to take place in a fluid-tight manner. There thus does not have to be a fluid-tight connection between the ejecting nozzle and the nozzle tube. Moreover, the funnel trap can be designed in such a manner that the latter can compensate tolerances in the positioning between the cleaning items carrier and the ejecting nozzle. Moreover, fluctuations in terms of positioning by virtue of the movement can be compensated, and a transmission of fluid across a comparatively long distance can also take place as a result of a corresponding geometric design embodiment of the funnel trap.

If a plurality of ejecting nozzles are provided, the latter can in each case be provided for different phases of the treatment, for example, for example in the respective treatment zones such as, for example, preliminary cleaning, primary cleaning, intermediate rinsing, disinfecting, clear-rinsing, blowing and drying. Alternatively or additionally, a plurality of ejecting nozzles can also be provided per treatment step.

If a plurality of ejecting nozzles are provided in the same treatment zone and/or in the same treatment phase, said ejecting nozzles can thus be passed sequentially by the cleaning items carrier, for example. As a result, an advantageous effect can be derived, for example by a pulsating impingement or else by an extended dwell time. Alternatively or additionally however, a plurality of ejecting nozzles can also be provided so as to be mutually parallel in the same treatment zone.

The funnel trap in terms of the geometry thereof can generally be adapted to the respective requirements. In this way, the entry opening can be designed having a circular shape, for example, or else be longitudinally oval, as explained above, for example. Other shapes are also possible, depending on the requirements. The entry opening can in particular be elongate, for example in the transport direction. In this way, a single ejecting nozzle can supply the fluid system of the cleaning items carrier with cleaning fluid on a longer stretch.

As explained above, the funnel trap can be disposed at different locations on the cleaning items carrier. Said funnel trap can thus be disposed on one or a plurality of sides selected from the lower side, the upper side or a lateral wall, for example the longitudinal side. The corresponding ejecting nozzles can be disposed in a corresponding manner within the conveyor washer. Furthermore, a plurality of different nozzle tubes, for example in the form of different fluid systems, can also be provided on or in the cleaning items carrier, for example for different treatment phases. These different nozzle tubes in this instance can be supplied from different ejecting nozzles of the conveyor washer, for example.

The at least one ejecting nozzle of the conveyor washer can be continuously supplied with the respective cleaning fluid, or the supply with the cleaning fluid can take place discontinuously, for example in a switched manner. In this way, an impingement of the at least one ejecting nozzle of the conveyor washer can in particular take place so as to be switched or controlled in a manner corresponding to at least one parameter selected from the group composed of: a position of the cleaning items carrier; a type of the cleaning items carrier; a type of the items to be cleaned. Alternatively or additionally, other parameters for switching or controlling the impingement of the at least one ejecting nozzle with cleaning fluid are also possible. As a result of this control of the impingement of the ejecting nozzle with cleaning fluid, special treatment sequences can generally be implemented, for example, and/or resources can be saved in that specific cleaning fluids are sprayed only when the latter are actually required, for example. The switching of the ejecting nozzles can take place, for example, by means of electromotive valves and/or electromagnetic valves. Purely mechanical solutions in which the cleaning items carrier per se interacts with an activation element, for example a sliding bracket, and opens a flap or a slide on the ejecting nozzle, for example, are also possible. Different design embodiments of a controlled impingement of the at least one ejecting nozzle with cleaning fluid are possible.

The at least one exit nozzle of the cleaning items carrier, for example the spray nozzle, can be individually configured, depending on the items to be cleaned. The design embodiment of the at least one exit nozzle can thus in particular be implemented in such a manner that the cleaning fluid dispensed by this exit nozzle is applied to the items to be cleaned with an ideally maximum effect. An internal structure to influence the flow of the cleaning fluid and/or to optimize the effect of the exit nozzle can also be incorporated within the nozzle tube and/or at the outlet of the exit nozzle. A geometry which generates a swirl in the fluid jet of the cleaning fluid and/or a mesh-type structure can thus be provided, for example.

Depending on the requirements set for the cleaning process, it can furthermore be helpful or necessary that it is known at which position within the conveyor washer the items to be cleaned, for example a mask, and/or the cleaning items carrier are/is situated. Different methods can be used for identifying and/or determining the position of the items to be cleaned and/or of the at least one cleaning items carrier in the conveyor washer. In this way, magnetic codes on the cleaning items carriers could thus be detected by way of corresponding sensors in the washer conveyor, for example. Alternatively or additionally, indicators made of metal and/or magnetic indicators on the cleaning items carriers, as well as corresponding sensors, could also be used. Again alternatively or additionally, inductive proximity sensors, RFID technology, light barriers, optical proximity sensors, technologies using optical image recognition, technologies using ultrasonic sensor arrays, cams and associated switches, or other technologies, could be used for identifying the items to be cleaned and/or the at least one cleaning items carrier.

As explained above, personal protective equipment in particular can be cleaned by means of the proposed cleaning items carrier and the proposed cleaning system. Harmful substances can be released in particular here, but also in other items to be cleaned, said harmful substances conjointly with the cleaning fluid being rinsed into at least one tank of the conveyor washer, for example. For example, a plurality of tanks which, for example by means of a cascading system, are disposed in series can be provided within the conveyor washer, so that the items to be cleaned initially pass one or a plurality of cleaning zones having a low degree of purity, for example, before passing through one or a plurality of cleaning zones having a higher degree of purity, for example a lower concentration of harmful substances. In this way, a washing tank can be configured so as to be sufficiently separated from at least one downstream clear-rinsing tank, for example, so that at least one clear-rinsing tank from which at least one pump clear-rinse is fed, for example, is not impinged with harmful substances from the wash tank. Furthermore, alternatively or additionally, two or more pump clear-rinses can be disposed in series, wherein the clear-rinsing tanks of these pump clear-rinses can be equipped with corresponding filter technology, for example.

The overall complexity in terms of equipment and personnel for cleaning items to be cleaned having at least one cavity at a high throughput can be significantly improved in comparison to conventional systems by means of the proposed cleaning items carrier and the proposed cleaning items system. Only one washer thus has to be typically provided for cleaning masks, for example, said washer being designed as a conveyor washer. The entire amount of items to be cleaned that arise can be treated with this conveyor washer.

Furthermore, the operation of the cleaning system can be designed so as to be significantly more economical than in conventional systems. In particular, the use of the conveyor washer can be designed so as to be significantly more economical in comparison to the use of a plurality of individual single-chamber washers. An efficient and economic flow of material can be set up here, and an efficient use of resources is made possible.

In summary, without any limitation in terms of further potential design embodiments, the following embodiments are proposed:

Embodiment 1: Cleaning items carrier for cleaning items to be cleaned having at least one cavity in a conveyor washer, in particular for cleaning cavities in personal protective equipment, comprising at least one base element as well as at least one nozzle tube connected to the base element, wherein the nozzle tube has at least one entry opening having at least one funnel trap, wherein the nozzle tube has at least one exit nozzle, and wherein the nozzle tube at least in portions tapers from the entry opening toward the exit nozzle.

Embodiment 2: Cleaning items carrier according to the preceding embodiment, wherein the cleaning items carrier is designed as an element selected from the group composed of: a chain link of a transport chain of a transport device of a conveyor washer; a cleaning basket, wherein the base element forms part of a basket base of the cleaning basket.

Embodiment 3: Cleaning items carrier according to any one of the preceding embodiments, wherein the cleaning items carrier furthermore has at least one flow-shaping element which is specified to shape a flow of the cleaning fluid exiting the exit nozzle, in particular at least one flow-shaping element selected from the group composed of: a funnel; a nozzle; a baffle; a pipeline, a swirl-inducing element.

Embodiment 4: Cleaning items carrier according to any one of the preceding embodiments, wherein the base element is at least in part configured as a chain link of a link chain, in particular having shaped elements in which are situated at least two, preferably four, bores through which the belt bars of the transport belt, or of the transport chain, respectively, can be guided.

Embodiment 5: Cleaning items carrier according to any one of the preceding embodiments, wherein the nozzle tube is designed so as to be funnel-shaped from the entry opening toward the exit nozzle.

Embodiment 6: Cleaning items carrier according to any one of the preceding embodiments, wherein the entry opening has an equivalent diameter which is larger than an equivalent diameter of the exit nozzle by a factor of at least 1.3, in particular by a factor of at least 1.5, in particular by a factor of at least 2.

Embodiment 7: Cleaning items carrier according to any one of the preceding claims, wherein the entry opening has a design selected from the group composed of: a circular design; an oval design, in particular an oval design having a longitudinal extent in a transport direction of the conveyor washer; a polygonal design.

Embodiment 8: Cleaning items carrier according to any one of the preceding embodiments, wherein the nozzle tube on a lower side of the base element terminates so as to be flush with the base element, wherein the nozzle tube on an upper side protrudes beyond the base element.

Embodiment 9: Cleaning items carrier according to any one of the preceding embodiments, wherein at least one entry opening is selected from the group composed of: an entry opening disposed on the lower side of the base element; an entry opening disposed on a longitudinal side of the base element; an entry opening disposed on an upper side of the base element.

Embodiment 10: Cleaning items carrier according to any one of the preceding embodiments, wherein the base element is at least in part designed as a mesh.

Embodiment 11: Cleaning items carrier according to any one of the preceding embodiments, wherein the nozzle tube is connected to a frame of the base element by mesh partitions.

Embodiment 12: Cleaning items carrier according to any one of the preceding embodiments, wherein the nozzle tube extends so as to be substantially perpendicular to the base element.

Embodiment 13: Cleaning items carrier according to any one of the preceding embodiments, wherein the base element is designed so as to be substantially flat, in particular plate-shaped.

Embodiment 14: Cleaning items carrier according to any one of the preceding embodiments, wherein at least one rack is attached to the base element.

Embodiment 15: Cleaning items carrier according to the preceding embodiment, wherein the rack forms a frame.

Embodiment 16: Cleaning items carrier according to any one of the two preceding embodiments, wherein the base element forms a flat bearing face.

Embodiment 17: Cleaning items carrier according to any one of the three preceding embodiments, wherein the rack is connected to the base element so as to be removable therefrom.

Embodiment 18: Cleaning items carrier according to any one of the preceding embodiments, wherein the rack forms at least one mounting for the items to be cleaned.

Embodiment 19: Cleaning items carrier according to the preceding embodiment, wherein the rack forms at least one mounting for a helmet and/or a respiratory mask.

Embodiment 20: Cleaning items carrier according to the preceding embodiment, wherein the rack furthermore has at least one mounting for a visor.

Embodiment 21: Cleaning items carrier according to any one of the preceding embodiments, furthermore comprising at least one closure element which is disposed so as to be movable in relation to the base element, wherein the closure element during the impingement with items to be cleaned is specified to close at least one opening of the items to be cleaned, in particular at least one opening selected from the group composed of an electrical connector opening and/or an airflow opening.

Embodiment 22: Cleaning items carrier according to the preceding embodiment, wherein the closure element is connected to the base element by way of at least one flexible connection element.

Embodiment 23: Cleaning items carrier according to any one of the preceding embodiments, wherein the cleaning items carrier has at least one identifier, in particular at least one identifier selected from the group composed of: a metallic identifier; an inductive identifier; an RFID identifier; a graphic identifier, in particular a barcode and/or QR code.

Embodiment 24: Cleaning system for cleaning items to be cleaned having at least one cavity, in particular for cleaning personal protective equipment, comprising:
I. at least one conveyor washer, comprising:
    at least one cleaning chamber;
    at least one impingement device for impinging the items to be cleaned in the cleaning chamber with at least one cleaning fluid;
    at least one transport device for transporting the items to be cleaned from an inlet of the conveyor washer, through the cleaning chamber, to an outlet of the conveyor washer; and
II. at least one cleaning items carrier according to one of the preceding embodiments, wherein the items to be cleaned are able to be received on the cleaning items carrier in such a manner that the cavity of the items to be cleaned is connected to the exit nozzle of the cleaning items carrier, wherein the cleaning items carrier by means of the transport device is transportable through the cleaning chamber, wherein the impingement device has at least one stationary ejecting nozzle, wherein the ejecting nozzle in at least one position of the cleaning items carrier is positioned relative to the cleaning items carrier in such a manner that cleaning fluid exiting the ejecting nozzle enters the funnel trap of the nozzle tube.

Embodiment 25: Cleaning system according to the preceding embodiment, wherein the conveyor washer has a plurality of ejecting nozzles.

Embodiment 26: Cleaning system according to the preceding embodiment, wherein at least two of the ejecting nozzles interact sequentially with the funnel trap.

Embodiment 27: Cleaning system according to any one of the embodiments relating to a cleaning system, wherein the cleaning items carrier has a plurality of entry openings, wherein the cleaning system is specified to have different entry openings fluidically interact with different ejecting nozzles, in particular so as to feed different entry openings with cleaning fluid from different ejecting nozzles in different treatment phases.

Embodiment 28: Cleaning system according to any one of the preceding embodiments relating to a cleaning system, wherein the conveyor washer is selected from the group composed of a belt conveyor washer and a basket conveyor washer.

Embodiment 29: Cleaning system according to any one of the embodiments relating to a cleaning system, wherein the conveyor washer has at least one sensor for identifying the cleaning items carrier.

Embodiment 30: Cleaning system according to the preceding embodiment, wherein the conveyor washer furthermore has a controller, wherein the controller is specified to control an impingement of the ejecting nozzle with cleaning fluid in a manner corresponding to the identification of the cleaning items carrier, in particular to activate only when a cleaning items carrier is situated in the region of the ejecting nozzle.

Embodiment 31: Cleaning system according to the preceding embodiment, wherein the conveyor washer has at least one valve and/or at least one switch for controlling the impingement with the cleaning fluid.

Embodiment 32: Cleaning system according to any one of the three preceding embodiments, wherein the sensor has at least one sensor selected from the group composed of: a sensor for identifying magnetic codes on the cleaning items carrier; a sensor for identifying identifiers made of metal on the cleaning items carrier; a reed switch; an inductive proximity sensor; an RFID sensor; a light barrier; an optical proximity sensor; an ultrasonic sensor; image recognition; an electromechanical switch, in particular an electromechanical switch for interacting with at least one cam on the cleaning items carrier.

Embodiment 33: Cleaning system according to any one of the preceding embodiments relating to a cleaning system, wherein the conveyor washer has a plurality of cleaning zones, wherein the cleaning zones are passed sequentially by the items to be cleaned.

Embodiment 34: Cleaning system according to the preceding embodiment, wherein the at least one stationary ejecting nozzle is disposed in at least one of the cleaning zones.

Embodiment 35: Cleaning system according to any one of the two preceding embodiments, wherein the cleaning zones have at least two cleaning zones selected from the group composed of: a preliminary clearing zone; a washing zone; a clear-rinsing zone, in particular a pump clear-rinsing zone and/or a fresh water clear-rinsing zone.

Embodiment 36: Cleaning system according to any one of the three preceding embodiments, wherein the conveyor washer furthermore has at least one drying zone disposed downstream of the cleaning zones.

Embodiment 37: Cleaning system according to the preceding embodiment, wherein at least one drying nozzle is disposed in the drying zone, wherein the drying nozzle in at least one position of the cleaning items carrier within the drying zone is positioned relative to the cleaning items carrier in such a manner that drying air exiting the drying nozzle enters the funnel trap of the nozzle tube.

Embodiment 38: Cleaning system according to any one of the preceding embodiments relating to a cleaning system, wherein the conveyor washer has a closed tank system, wherein the closed tank system is connected to at least one waste disposal tank for disposing hazardous waste.

Embodiment 39: Cleaning system according to any one of the preceding embodiments relating to a cleaning system, wherein the conveyor washer has at least one filter system for the post-impingement filtering, of the items to be cleaned, of toxic substances from the cleaning fluid.

Embodiment 40: Cleaning system according to any one of the preceding embodiments relating to a cleaning system, wherein the ejecting nozzle is disposed below the transport device so as to point upward, wherein the final trap of the nozzle tube is aligned so as to point downward, wherein the cleaning fluid exiting the ejecting nozzle enters the funnel trap of the nozzle tube when the funnel trap and the ejecting nozzle are congruent.

Embodiment 41: Cleaning system according to any one of the preceding embodiments relating to a cleaning system, wherein the ejecting nozzle and the nozzle tube pass one another without contact.

Embodiment 42: Cleaning system according to any one of the preceding embodiments relating to a cleaning system, wherein the transport device is selected from the group composed of: a transport belt, wherein the cleaning items carrier, in particular as a basket-shaped cleaning items carrier, is placed on the transport belt; a transport belt, wherein the cleaning items carrier, in particular as a basket-shaped cleaning items carrier, is connected, in particular latched, to the transport belt; as a link chain, wherein the cleaning items carrier, in particular as a chain link, is incorporated in the link chain; a latching transport system, wherein the cleaning items carrier, in particular as a basket-shaped cleaning items carrier, is able to be placed in particular on sliding elements of the latching transport system.

Embodiment 43: Cleaning system according to any one of the preceding embodiments relating to a cleaning system, wherein the ejecting nozzle is designed to be variable, in particular in terms of the jet direction thereof and/or in terms of the jet shape thereof.

Embodiment 44: Cleaning system according to the preceding embodiment, wherein the cleaning system is specified to automatically vary the ejecting nozzle.

Embodiment 45: Method for cleaning items to be cleaned having at least one cavity, while using at least one cleaning system according to any one of the preceding embodiments relating to a cleaning system, comprising the following steps:
i) receiving the items to be cleaned on the cleaning items carrier in such a manner that the cavity of the items to be cleaned by means of the exit nozzle of the cleaning items carrier is able to be impinged with at least one cleaning fluid;
ii) transporting the cleaning items carrier through the cleaning chamber by means of the transport device; and
iii) impinging the items to be cleaned with at least one cleaning fluid by means of the impingement device, wherein in at least one position of the cleaning items carrier relative to the ejecting nozzle, cleaning fluid exiting the ejecting nozzle enters the funnel trap of the nozzle tube, passes through the nozzle tube, and from the exit nozzle of the nozzle tube enters the cavity of the items to be cleaned.

Embodiment 46: Method according to the preceding embodiment, wherein the cleaning items carrier is populated with the items to be cleaned outside the conveyor washer, and in the populated form is then introduced into the conveyor washer.

Embodiment 47: Method according to any one of the preceding embodiments relating to a method, wherein the cleaning items carrier is configured in multiple parts, wherein the transport device is configured as a revolving transport device, wherein the cleaning items carrier conjointly with the items to be cleaned is transported through the cleaning chamber by means of the transport device, wherein the items to be cleaned as well as a part of the cleaning items carrier are subsequently removed, and wherein a further part of the cleaning items carrier, in particular the base element, by means of the transport device is transported back to the inlet.

Embodiment 48: Method according to any one of the preceding embodiments relating to a method, wherein the items to be cleaned are fixed in the cleaning items carrier in such a manner that the at least one cavity of the items to be cleaned is positioned so as to be locationally fixed in relation to the exit nozzle.

Embodiment 49: Method according to any one of the preceding embodiments relating to a method, wherein the items to be cleaned have at least one helmet having at least one visor, wherein the helmet is fixed in the cleaning items carrier, wherein the visor furthermore is fixed at a predefined angular position in the cleaning items carrier.

Embodiment 50: The use of the cleaning items carrier according to any one of the preceding embodiments relating to a cleaning items carrier and/or of the cleaning system according to any one of the preceding embodiments relating to a cleaning system, for cleaning personal protective equipment.

Embodiment 52: The use according to the preceding embodiment, wherein the personal protective equipment is selected from the group composed of: a respiratory mask; a helmet having at least one airflow duct.

BRIEF DESCRIPTION OF THE FIGURES

Further details and features are derived from the description hereunder of exemplary embodiments, in particular in conjunction with the dependent claims. The respective features here can be implemented individually or in combination with one another. The invention is not limited to the exemplary embodiments. The exemplary embodiments are schematically illustrated in the figures. The same reference signs in the individual figures here refer to identical or functionally identical or functionally equivalent elements.

In the figures:

FIGS. 2 to 4 show different illustrations of a first exemplary embodiment of a cleaning items carrier;

DESCRIPTION OF THE EXEMPLARY EMBODIMENTS

Figure 1:
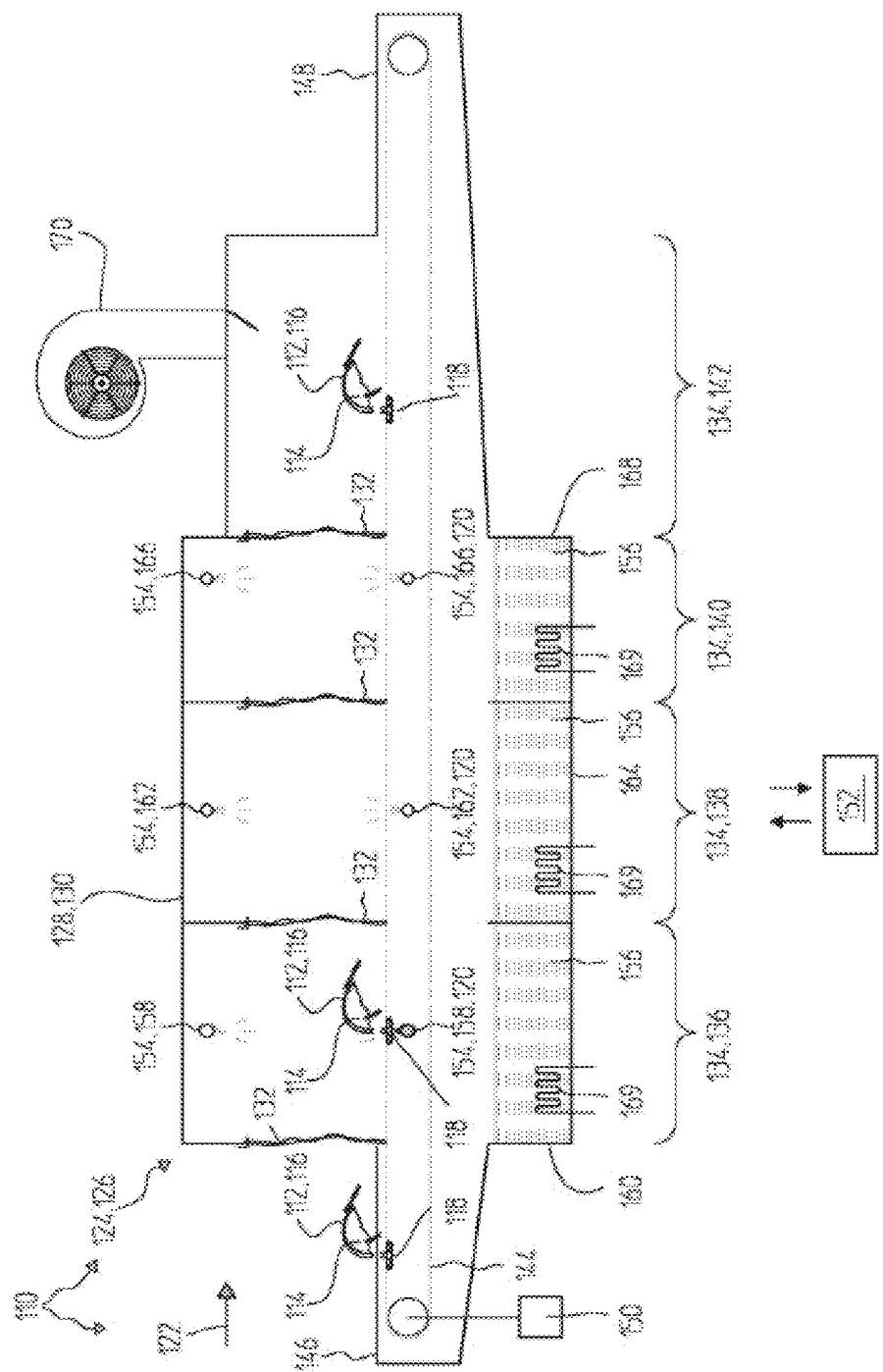
FIG. 1 shows a first exemplary embodiment of a cleaning system for cleaning items to be cleaned having at least one cavity, in a lateral sectional illustration.
Figure 2:
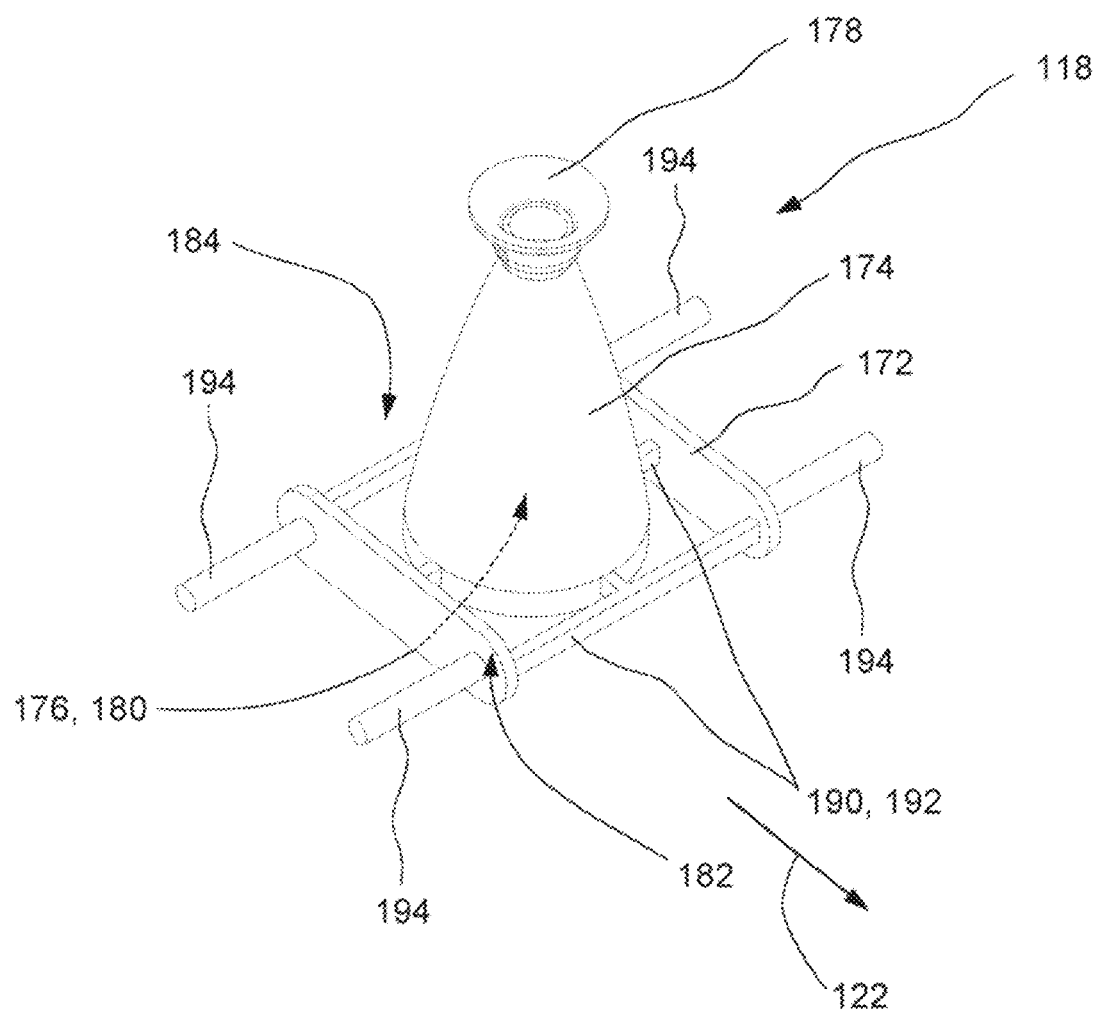

Shown in FIG. 1 is a first exemplary embodiment of a cleaning system 110 for cleaning items to be cleaned 112 having at least one cavity 114. The items to be cleaned 112 in this exemplary embodiment are illustrated in an exemplary manner as a helmet 116 of personal protective equipment. The items to be cleaned 112 are received on the cleaning items carriers 118 which are shown in an exemplary manner in a first exemplary embodiment in FIGS. 2, 3 and 4. FIG. 2 here shows a perspective illustration of a cleaning items carrier 118, FIG. 3 shows a sectional illustration through the cleaning items carrier 118, as well as an ejecting nozzle 120 which is yet to be explained in more detail hereunder, in a section parallel to a transport direction 122 of the cleaning system 110, and FIG. 4 shows the assembly according to FIG. 3 in a sectional illustration having the section plane perpendicular to the transport direction 122. FIGS. 1 to 4 will be conjointly explained hereunder.

The cleaning system 110 in this exemplary embodiment, apart from a plurality of cleaning items carriers 118, comprises a conveyor washer 124. This conveyor washer 124 in the exemplary embodiment illustrated is designed in an exemplary manner as a belt conveyor washer 126, also referred to as a belt transport conveyor washer. Said belt conveyor washer 126 has a cleaning chamber 128 in the form of a cleaning tunnel 130. The cleaning tunnel 130, in particular by way of separation curtains 132, can be divided into a plurality of zones 134, also referred to as cleaning zones, wherein in an exemplary manner a preliminary clearing zone 136, a rinsing zone 138, also referred to as the washing zone, a clear-rinsing zone 140, also referred to as the post-rinsing zone, and a drying zone 142 are provided in the illustrated exemplary embodiment. The clear-rinsing zone 140 can yet again be divided into a pump clear-rinsing zone and a fresh water clear-rinsing zone, for example. Another design embodiment of the zones 134 is also possible.

In the exemplary embodiment illustrated, items to be cleaned 112, for example in the form of items of personal protective equipment, are conveyed in the transport direction 122 through the cleaning tunnel 130 by means of at least one transport device 144. For this purpose, the conveyor washer 124 can be designed, for example, as a belt conveyor machine 126, as is shown in FIG. 1, or else as a basket conveyor machine as will yet be shown in more detail hereunder by means of FIG. 6. For example, at least one inlet or inlet region 146, where the items to be cleaned 112 are loaded on the transport device 144, and at least one outlet or outlet region 148, where the cleaned items to be cleaned 112 can be retrieved, can be provided. Accordingly, the transport device 144 can comprise at least one belt and/or at least one link chain, for example. Other design embodiments are also possible. The transport device 144 can comprise, for example, at least one drive 150, for example a motor, which can be actuated by way of a controller 152, for example.

The items to be cleaned 112 in the zones 136, 138 and 140 by means of at least one impingement device 154 can be impinged with at least one cleaning fluid 156, for example at least one cleaning liquid. For this purpose, at least one preliminary clearing zone nozzle system 158 can be provided in the preliminary clearing zone 136, for example, said preliminary clearing zone nozzle system 158 being able to be fed from a preliminary clearing tank 160 with cleaning fluid 156 by way of a pump, not illustrated in FIG. 1, and a line system, not illustrated, for example. For example, a rinsing zone nozzle system 162 can be provided in the rinsing zone 136, said rinsing zone nozzle system 162 being able to be fed with cleaning fluid 156 from a rinsing tank 164, also referred to as the washing tank, by way of a pump, likewise not illustrated, and a line system, likewise not illustrated, for example. For example, at least one post-rinsing nozzle system 166, also referred to as the clear-rinsing nozzle system, which can be fed with cleaning fluid 156 in the form of heated freshwater, for example, and/or with post-rinsing fluid from a post-rinsing tank 168, also referred to as the clear-rinsing tank, can be provided in the clear-rinsing zone 140, the latter potentially being designed integrally or else in multiple parts. Heating devices 169 can be provided in the tanks 160, 164 and 168, for example. Furthermore, filter devices can also be provided in these tanks 160, 164 and 168, for example so as to have the effect of purifying the cleaning fluid 156 in the case of a recirculating operation. Furthermore, the tanks 160, 164 and 168 can be provided with a cascade overflow and/or a pumped cascade, so that the highest degree of purity prevails in the post-rinsing tank 168, and the lowest degree of purity prevails in the preliminary clearing tank 160, for example.

After passing through the zones 136, 138 and 140, the items to be cleaned 112 can then enter the drying zone 142 in which the items to be cleaned 112 can be impinged with hot air, for example by way of a blower 170, so as to accelerate the drying of the items to be cleaned 112. The outlet region 148 in the transport direction 122 is disposed downstream of the cleaning chamber 128 so that the cleaned items to be cleaned 112 in the outlet region 148 can be retrieved from the transport device 144.

In the conveyor washer 124 illustrated, there is fundamentally the principle that the impingement device 154 is designed to be locationally fixed, whereas the items to be cleaned 112 are removed in the transport direction 122 relative to this impingement device 154. This cleaning principle, in particular in the case of items to be cleaned 112 having at least one cavity 114, can lead to challenges in terms of an insufficient quantity of cleaning fluid 156 making its way into the cavity 114. The cavity 114 can in particular be an elongate cavity, for example at least one air duct, as will yet be explained in more detail hereunder using the example of FIG. 6. The nozzles of the impingement device 154 typically pass the cavity 114 and/or an entry opening of this cavity 114 too fast to allow a sufficient amount of cleaning fluid to make its way into this cavity 114. Furthermore, the cavity 114 in many cases is obscured by component parts of the transport device 144. In order for this set of problems to be solved, it is proposed in the exemplary embodiment illustrated in FIGS. 2 to 4 that the cleaning items carrier 118 has at least one base element 172, as well as furthermore at least one nozzle tube 174 connected to the base element 172. The nozzle tube 174 is thus integrated in the movable cleaning items carrier 118, said nozzle tube 114 being able to act as a movable cleaning nozzle and to provide a duct structure for a fluid flow. The nozzle tube 174 has at least one entry opening 176 as well as at least one exit nozzle 178, also referred to as the exit opening. The exit nozzle 178 acts as a cleaning nozzle which is movable in the cleaning chamber 128 and transported by the transport device 144. The nozzle tube 174 on the entry opening 176 thereof has a funnel trap 180 so that the nozzle tube 174 in the interior thereof, at least in portions, is configured so as to taper. In particular, the entry opening 176 can have a significantly larger diameter or equivalent diameter than the exit nozzle 178. In this way, the nozzle tube 174 is designed such that the effective cross section on the side of the entry opening 176 for trapping cleaning fluid 156 is significantly larger than the diameter or equivalent diameter of the exit nozzle 178 and/or than a diameter of the at least one cavity 114 of the items to be cleaned 112, or an entry opening of this cavity 114. In comparison to a situation in which the impingement device 154 would inject directly into the cavity 114, the effective cross section for the invasion of cleaning fluid 156 into the cavity 114 is thus significantly increased as a result of the funnel trap 180.

In the exemplary embodiment illustrated, for example, the nozzle tube 174 is received in the base element 172 in such a manner that the entry opening 176 is disposed on a lower side 182 of the base element 172, while the exit nozzle 178 is disposed on an upper side 184 of the base element 172. For example, the base element 172 on the upper side 184 can have a rack 186 which forms a completely or partially encircling frame 188, for example. The items to be cleaned 112 can be fastened or clamped to this frame 188 so that at least one opening of the cavity 114 comes to be congruent with the exit nozzle 178, for example. As can be seen in FIGS. 3 and 4, the impingement device 154 can comprise, for example, the at least one ejecting nozzle 120, which may be a component part of a lower nozzle system of the conveyor washer 124 according to FIG. 1, for example. As can be seen in FIGS. 3 and 4, this ejecting nozzle 120 can be aligned upward, for example. As soon as the entry opening 176 is congruent with the at least one ejecting nozzle 120, cleaning fluid 156 exiting the ejecting nozzle 120 can enter the funnel trap 180 and, by virtue of the impetus thereof, can exit the exit nozzle 178 on the upper side 184 and be injected into the cavity 114 of the items to be cleaned 112. A further impingement from one or a plurality of spatial directions can take place simultaneously or temporally offset from other nozzles of the impingement device 154 so that, in addition to the cavity 114, at least one surface of the items to be cleaned 112 can also be cleaned by cleaning fluid 156.

The disposal of the entry opening 176 on the lower side 182 of the base element 172 is fundamentally preferable, because the cleaning fluid 156 upon impingement of the cavity 114 in this instance can run off toward the bottom again, said cleaning fluid 156 being driven by the gravity thereof. Alternatively or additionally however, other possibilities are also conceivable. In this way, the entry opening 176 can also be disposed on at least one lateral wall of the base element 172, for example on at least one longitudinal side and/or else on the upper side 184. Furthermore, one or else a plurality of entry openings 176 can be provided. The entry opening 176 can be designed to be circular, for example. Alternatively however, a design embodiment in which an extent in the transport direction 122 is longer than transversely to the transport direction 122 can also be possible, so that cleaning fluid 156 can be trapped by the funnel trap 180 over a longer distance. As a result, the impingement duration can be extended.

The at least one nozzle tube 174 can penetrate the base element 172, for example, and/or can be held in the base element 172 or on the base element 172 in another way. For example, as can be seen in FIG. 2, the base element 172 can be designed as a mesh 190 and can have a plurality of mesh partitions 192 which connect the nozzle tube 174 to the frame 188. In this way, cleaning fluid can run off toward the bottom through the base element 172.

As explained above, the transport device 144 of the conveyor washer 124 can in particular be designed as a belt or as a link chain. The base element 172 can be integratable in the transport device 144, for example, and/or be, preferably reversibly, connectable to the transport device 144. The base element 172 can thus be configured as the chain link of a link chain, for example having bores through which belt bars 194 of the transport device are guided, for example, said belt bars then extending onward on both sides.

The cleaning items carrier 118 can be integrally designed or else in multiple parts. In this way, the rack 186 can be completely or partially removable from the base element 172, for example. For example, the removable part can be connected to the items to be cleaned 112 and be removed from the transport device 144 in the outlet region 148.

Figure 5:
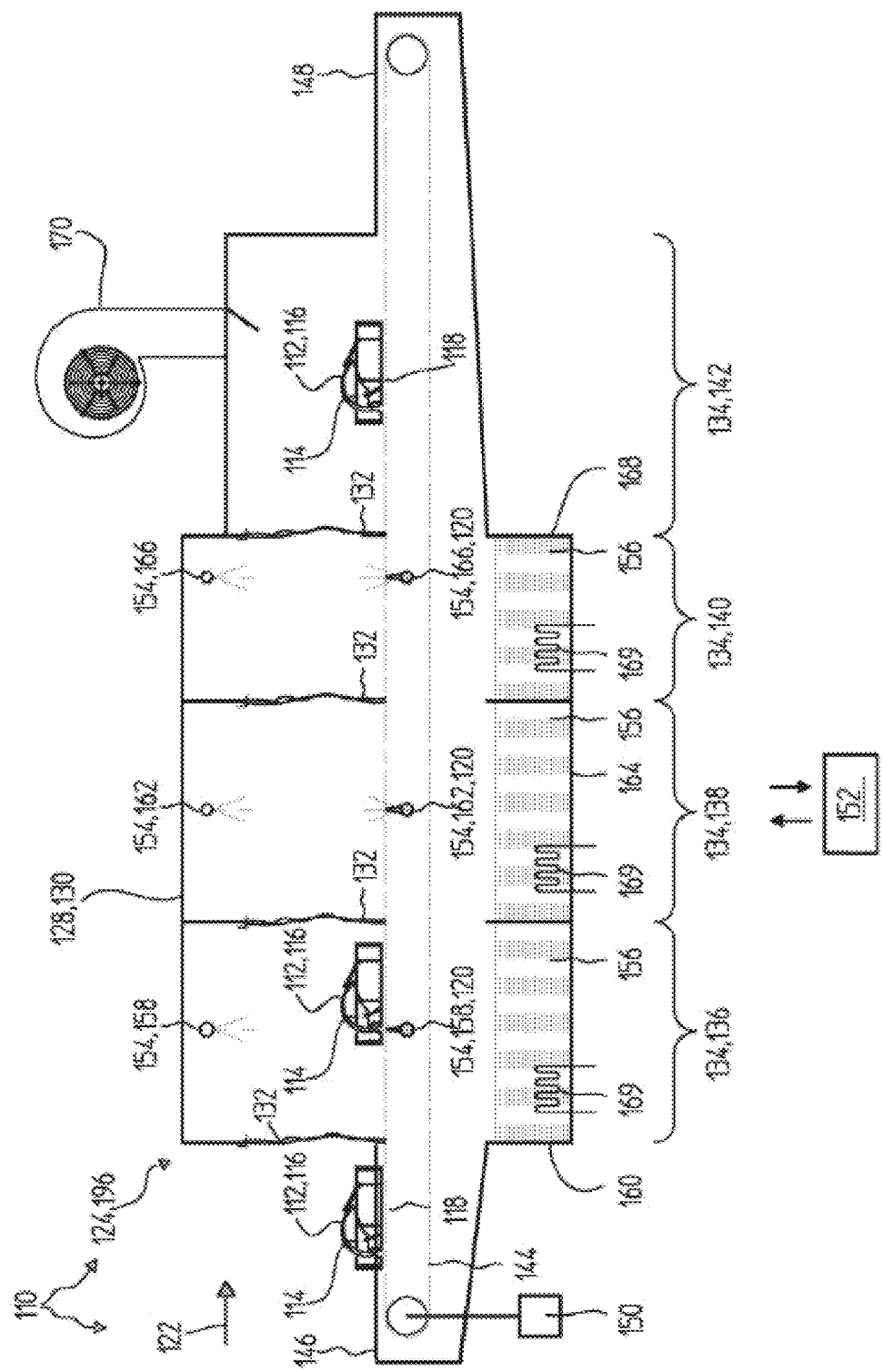
FIG. 5 shows a second exemplary embodiment of a cleaning system for cleaning items to be cleaned having at least one cavity, in a lateral sectional illustration.
Figure 6:
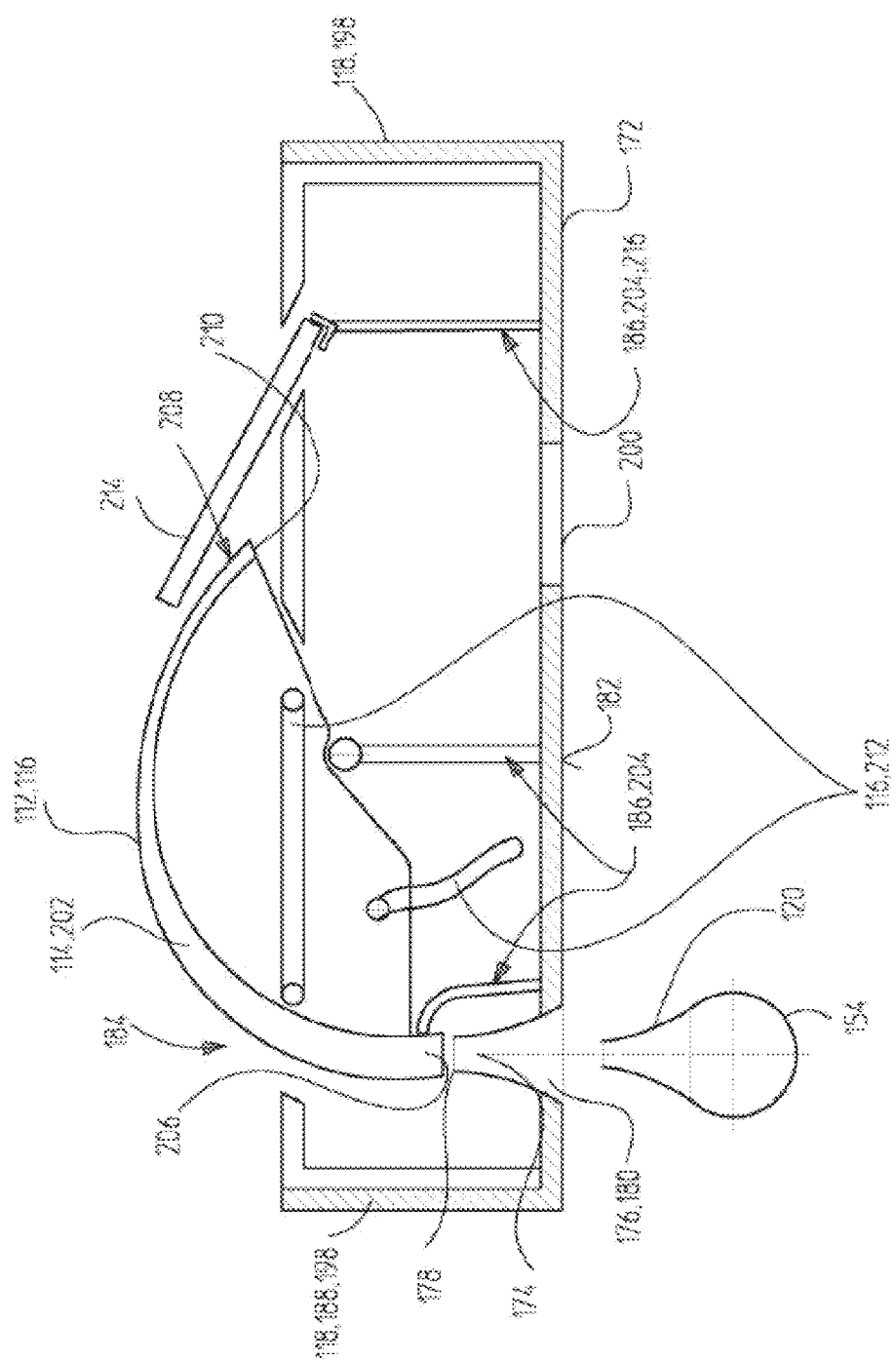
FIG. 6 shows a second exemplary embodiment of a cleaning items carrier designed as a cleaning basket, in a lateral sectional illustration.

In the exemplary embodiment according to FIG. 1, the conveyor washer 124 in an exemplary manner is designed as a belt washer 126. The cleaning items carrier 118 can accordingly be configured as a device which is integratable in a belt or a link chain of the transport device 144, for example as a chain link and/or which is connectable, for example reversibly, for example by way of a form-fitting and/or force-fitting connection, to the belt or the link chain of the transport device 144. As an alternative to an integration in a belt, the cleaning items carrier 118 can thus also be hooked or latched into this belt, for example. Alternatively however, the conveyor washer 124 can also be designed in another way, for example as a basket conveyor washer 196. This is shown in an exemplary manner in FIGS. 5 and 6. In a manner analogous to FIG. 1, FIG. 5 here shows an exemplary embodiment of a conveyor washer 124, designed as a basket conveyor washer 196, in a sectional illustration having the section plane parallel to a transport direction 122. FIG. 6 in a corresponding manner shows a sectional illustration through a cleaning items carrier 118, designed as a cleaning basket 198, for use in the basket conveyor washer 196 according to FIG. 5. Both figures will be conjointly described hereunder.

The cleaning system 110 according to FIG. 5 again has, as described above, a conveyor washer 124 and a plurality of cleaning items carriers 118. The conveyor washer 124 in the exemplary embodiment illustrated is designed as a basket conveyor washer 196, and the cleaning items carriers 118 are designed as cleaning baskets 198. Accordingly, the transport device 144 can in particular be designed as a transport belt for the cleaning baskets 198, the cleaning baskets 198 being able to be placed on said transport belt. In terms of the potential design embodiments and the elements of the conveyor washer 124, reference otherwise can largely be made to the description of FIG. 1.

Shown in FIG. 6 is an exemplary embodiment of a cleaning basket 198 in a sectional illustration. The cleaning basket 198 again comprises a base element 172 which can be designed as a basket base, for example. A plurality of openings 200 through which cleaning fluid from the cleaning basket 198 can run off can be provided in the base element 172. Furthermore, at least one nozzle tube 174 is again provided, which again on a lower side 182 of the cleaning items carrier 118 and/or of the base element 172 can have an entry opening 176, for example. Again provided are moreover a funnel trap 180 as well as an exit nozzle 178, wherein reference may be made to the description of FIGS. 2 to 4. A design embodiment in a manner analogous to these figures is also fundamentally possible in FIG. 6. Furthermore, it is also possible for the entry opening 176 to be placed on a side other than the lower side 182, wherein a placing on the lower side 182 however may have the advantages described above.

As can be seen in FIG. 6, the items to be cleaned 112 can comprise elements of personal protective equipment, for example. Illustrated in an exemplary manner here is again a helmet 116 which can have respiratory protective function. This helmet 116 can have at least one cavity 114 which is shown in a sectional illustration in FIG. 6. This cavity 114 can be designed, for example, as an airflow duct 202, also referred to as the breathing air duct. This airflow duct 202 can be specified for supplying breathing air and/or for discharging exhaled air, wherein one or a plurality of ducts of this type can be provided.

At least one rack 186 can again be provided on the base element 172. On the one hand, this rack 186 can form or comprise a frame 188, for example, which can form a basket wall of the cleaning basket 198, for example. Furthermore, the rack 186 can form or comprise at least one mounting 204 for the items to be cleaned 112, for example. By means of this mounting 204, the items to be cleaned 112 can be fixed in such a manner, for example, that at least one inlet opening 206 of the cavity 114, for example of the airflow duct 202, comes to be congruent with the exit nozzle 178, as can be seen in FIG. 6. In this way, cleaning fluid exiting the ejecting nozzle 120 can be injected into the inlet opening 206 of the cavity 114, for example. Moreover, the cavity 114, for example on an end side 208 of the helmet 116, can have at least one outlet opening 210. The injected cleaning fluid can exit the cavity 114 again from this outlet opening 210, or else from the inlet opening 206. In this way, the cavity 114 can generally have at least one opening.

Apart from the function of fixing the items to be cleaned 112 relative to the exit nozzle 178, fixing of the items to be cleaned 112 can also be performed in another way. A strapping 212 of the helmet 116 can thus be held by the mounting 204, for example. Again alternatively or additionally, the helmet 116 can also have at least one visor 214, for example, which for cleaning can be held in a specific position. In this way, the rack 186 can have at least one mounting 216 for the visor 214, for example, which mounting 216 can hold the visor 214 in a predefined position, for example at a predefined angular position, during cleaning.

Figure 7:
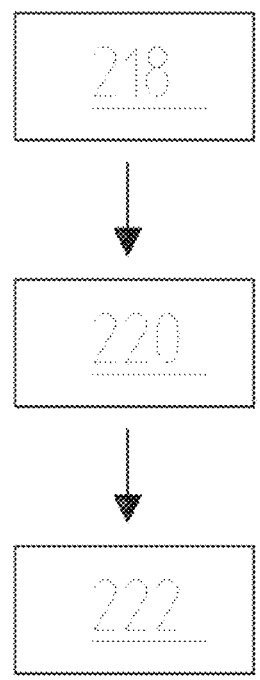
FIG. 7 shows a schematic flow diagram of an exemplary embodiment of a method according to the invention for cleaning items to be cleaned having at least one cavity.

A schematic flowchart of an exemplary embodiment of a method for cleaning items to be cleaned 112 having at least one cavity 114 is shown in FIG. 7. The method comprises the use of a cleaning system 110 according to the invention, for example according to FIG. 1 or according to FIG. 5. Accordingly, reference in terms of potential design embodiments can largely be made to the above description of these figures.

In the exemplary embodiment illustrated the method comprises receiving the items to be cleaned 112 in the cleaning items carrier 118 in such a manner that the cavity 114 of the items to be cleaned 112 by means of the exit nozzle 178 of the nozzle tube 174 is able to be impinged with the at least one cleaning fluid 156 (step 218). As explained above, this can take place in that at least one inlet opening 206 of the cavity 114 is brought to be congruent with the exit nozzle 178.

The method according to FIG. 7 furthermore comprises transporting the cleaning items carrier 118 through the cleaning chamber 128 by means of the transport device 144 (step 220).

The method according to FIG. 7 furthermore comprises impinging the items to be cleaned 112 with the at least one cleaning fluid 156 by means of the impingement device 154 (step 222). This impingement takes place in such a manner that in at least one position of the cleaning items carrier 118 relative to the at least one ejecting nozzle 120, cleaning fluid 156 exiting the ejecting nozzle 120 enters the funnel trap 180 of the nozzle tube 174, said cleaning fluid 156 in particular being injected into the latter. Furthermore, the impingement takes place in such a manner that this cleaning fluid 156 passes through the nozzle tube 174, and from the exit nozzle 178 of the nozzle tube 174 enters the cavity 114 of the items to be cleaned 112, said cleaning fluid 156 in particular being injected into this cavity. This impingement can take place in particular during a movement of the transport device 144.

LIST OF REFERENCE SIGNS

110 Cleaning system
112 Items to be cleaned
114 Cavity
116 Helmet
118 Cleaning items carrier
120 Ejecting nozzle
122 Transport direction
124 Conveyor washer
126 Belt washer
128 Cleaning chamber
130 Cleaning tunnel
132 Separation curtain
134 Zone
136 Preliminary clearing zone
138 Washing zone
140 Clear-rinsing zone
142 Drying zone
144 Transport device
146 Inlet region
148 Outlet region
150 Drive
152 Controller
154 Impingement device
156 Cleaning fluid
158 Preliminary clearing zone nozzle system 160 Preliminary clearing tank
162 Washing zone nozzle system
164 Rinsing tank
166 Post-rinsing nozzle system
168 Post-rinsing tank
169 Heating device
170 Blower
172 Base element
174 Nozzle tube
176 Entry opening
178 Exit nozzle
180 Funnel trap
182 Lower side
184 Upper side
186 Rack
188 Frame
190 Mesh partition
194 Belt bar
196 Basket conveyor washer
198 Cleaning basket
200 Opening
202 Airflow duct
204 Mounting
206 Inlet opening
208 End side
210 Outlet opening
212 Strapping
214 Visor
216 Mounting for visor
218 Receiving the cleaning items on the cleaning items carrier
220 Transporting the cleaning items carrier through the cleaning chamber
222 Impinging the cleaning items with at least one cleaning fluid

The invention claimed is:

1. A method for cleaning items to be cleaned in the form of personal protective equipment selected from the group consisting of a respirator mask and a helmet having at least one air-guiding duct, wherein the items to be cleaned have at least one cavity,
wherein at least one cleaning system comprising the following is used:
I. at least one conveyor washer, comprising:
at least one cleaning chamber,
at least one impingement device for impinging the items to be cleaned in the cleaning chamber with at least one cleaning fluid;
at least one transport device for transporting the items to be cleaned from an inlet of the conveyor washer, through the cleaning chamber, to an outlet of the conveyor washer; and
II. at least one cleaning items carrier comprising at least one base element as well as at least one nozzle tube connected to the base element, wherein the nozzle tube has at least one entry opening having at least one funnel trap, wherein the nozzle tube has at least one exit nozzle and wherein the nozzle tube at least in portions tapers from the entry opening toward the exit nozzle,
wherein the items to be cleaned are able to be received on the cleaning items carrier in such a manner that the cavity of the items to be cleaned is connected to the exit nozzle of the cleaning items carrier, wherein the cleaning items carrier by means of the transport device is transportable through the cleaning chamber, wherein the impingement device has at least one stationary ejecting nozzle, wherein the ejecting nozzle in at least one position of the cleaning items carrier is positioned relative to the cleaning items carrier in such a manner that cleaning fluid exiting the ejecting nozzle enters the funnel trap of the nozzle tube, wherein at least one rack is attached to the base element, wherein the rack forms at least one mounting for the items to be cleaned, wherein the items to be cleaned by means of the mounting are fixed in such a manner that at least one inlet opening of the cavity comes to be congruent with the exit nozzle, wherein cleaning fluid exiting the ejecting nozzle is injected into the inlet opening of the cavity, wherein the cavity furthermore has at least one outlet opening, wherein the injected cleaning fluid exits the cavity again from this outlet opening or from the inlet opening; wherein the method comprises the following steps:
i) receiving the items to be cleaned on the cleaning items carrier in such a manner that the cavity of the items to be cleaned by means of the exit nozzle of the cleaning items carrier is able to be impinged with at least one cleaning fluid;
ii) transporting the cleaning items carrier through the cleaning chamber by means of the transport device; and
iii) impinging the items to be cleaned with at least one cleaning fluid by means of the impingement device, wherein in at least one position of the cleaning items carrier relative to the ejecting nozzle, cleaning fluid exiting the ejecting nozzle enters the funnel trap of the nozzle tube, passes through the nozzle tube, and from the exit nozzle of the nozzle tube enters the cavity of the items to be cleaned.

2. The method as claimed in claim 1, wherein the items to be cleaned are positioned with an opening of the cavity in front of the exit nozzle.

3. The method as claimed in claim 1, wherein the cleaning items carrier is configured in multiple parts, wherein the transport device is configured as a revolving transport device, wherein the cleaning items carrier conjointly with the items to be cleaned by means of the transport device is transported through the cleaning chamber, wherein the items to be cleaned as well as one part of the cleaning items carrier are subsequently removed, and wherein a further part of the cleaning items carrier by means of the transport device is transported back to the inlet.

4. The method as claimed in claim 1, wherein the items to be cleaned are fixed in the cleaning items carrier in such a manner that the at least one cavity of the items to be cleaned is positioned so as to be locationally fixed in relation to the exit nozzle.

5. The method as claimed in claim 1, wherein the items to be cleaned have at least one helmet having at least one visor, wherein the helmet is fixed in the cleaning items carrier, wherein the visor in the cleaning items carrier is furthermore fixed at a predefined angular position.

6. The method as claimed in claim 1, wherein the conveyor washer has a plurality of ejecting nozzles, wherein at least two of the ejecting nozzles interact sequentially with the funnel trap.

7. The method as claimed in claim 1, wherein the conveyor washer has at least one sensor for identifying the cleaning items carrier, wherein the conveyor washer furthermore has a controller, wherein the controller is specified to control an impingement of the ejecting nozzle with a cleaning fluid in a manner corresponding to the identification of the cleaning items carrier.

8. The method as claimed in claim 1, wherein the conveyor washer has a plurality of cleaning zones, wherein the cleaning zones are passed sequentially by the items to be cleaned, wherein the at least one stationary ejecting nozzle is disposed in at least one of the cleaning zones, wherein the conveyor washer furthermore has at least one drying zone which is disposed downstream of the cleaning zones, wherein at least one drying nozzle is disposed in the drying zone, wherein the drying nozzle in at least one position of the cleaning items carrier within the drying zone is positioned relative to the cleaning items carrier in such a manner that drying air exiting the drying nozzle enters the funnel trap of the nozzle tube.

9. The method as claimed in claim 1, wherein the transport device is selected from the group consisting of: a transport belt, wherein the cleaning items carrier is placed onto the transport belt; a transport belt, wherein the cleaning items carrier is connected to the transport belt; a link chain, wherein the cleaning items carrier is inserted as a chain link in the link chain; a latching transport system, wherein the cleaning items carrier is able to be placed on sliding elements of the latching transport system.

10. The method as claimed in claim 1, wherein the ejecting nozzle is designed to be variable.

11. A cleaning items carrier for use in the method as claimed in claim 1, comprising at least one base element as well as at least one nozzle tube connected to the base element, wherein the nozzle tube has at least one entry opening having at least one funnel trap, wherein the nozzle tube has at least one exit nozzle and wherein the nozzle tube at least in portions tapers from the entry opening toward the exit nozzle, wherein at least one rack is attached to the base element, wherein the rack forms at least one mounting for the items to be cleaned, wherein the items to be cleaned by means of the mounting are able to be fixed in such a manner that at least one inlet opening of the cavity comes to be congruent with the exit nozzle.

12. A cleaning system for carrying out the method as claimed in claim 1, comprising:
   I. at least one conveyor washer, comprising:
      at least one cleaning chamber;
      at least one impingement device for impinging the items to be cleaned in the cleaning chamber with at least one cleaning fluid;
      at least one transport device for transporting the items to be cleaned from an inlet of the conveyor washer, through the cleaning chamber, to an outlet of the conveyor washer; and
   II. at least one cleaning items carrier as claimed in claim 1, wherein the items to be cleaned are able to be received on the cleaning items carrier in such a manner that the cavity of the items to be cleaned is connected to the exit nozzle of the cleaning items carrier, wherein the cleaning items carrier by means of the transport device is transportable through the cleaning chamber, wherein the impingement device has at least one stationary ejecting nozzle, wherein the ejecting nozzle in at least one position of the cleaning items carrier is positioned relative to the cleaning items carrier in such a manner that cleaning fluid exiting the ejecting nozzle enters the funnel trap of the nozzle tube.

\* \* \* \* \*